US011479879B2

(12) United States Patent
Pajuelo et al.

(10) Patent No.: US 11,479,879 B2
(45) Date of Patent: Oct. 25, 2022

(54) TRIPLE VECTOR FOR EXPRESSING ANTIBODY MOLECULES IN FULL THERAPEUTIC FORMAT

(71) Applicants: argenx BV, Ghent (BE); Fairjourney Biologics, Oporto (PT)

(72) Inventors: Maria Gonzalez Pajuelo, Oporto (PT); Johannes Joseph Wilhelmus De Haard, Oudelande (NL)

(73) Assignees: argenx BV, Ghent (BE); FAIRJOURNEY BIOLOGICS, Porto, PR (US)

( * ) Notice: Subject to any disclaimer, the term of this patent is extended or adjusted under 35 U.S.C. 154(b) by 789 days.

(21) Appl. No.: 16/337,815

(22) PCT Filed: Oct. 11, 2017

(86) PCT No.: PCT/EP2017/075983
§ 371 (c)(1),
(2) Date: Mar. 28, 2019

(87) PCT Pub. No.: WO2018/069416
PCT Pub. Date: Apr. 19, 2018

(65) Prior Publication Data
US 2019/0225672 A1    Jul. 25, 2019

(30) Foreign Application Priority Data

Oct. 11, 2016 (GB) ..................................... 1617270

(51) Int. Cl.
*C40B 40/08* (2006.01)
*C12N 15/63* (2006.01)
(Continued)

(52) U.S. Cl.
CPC ............ *C40B 40/08* (2013.01); *C07K 16/005* (2013.01); *C12N 15/63* (2013.01); *C12N 15/70* (2013.01);
(Continued)

(58) Field of Classification Search
None
See application file for complete search history.

(56) References Cited

FOREIGN PATENT DOCUMENTS

| WO | WO 02/061090 A2 | 8/2002 |
| WO | WO 2004/063343 A2 | 7/2004 |
| WO | WO 2014/008391 A1 | 1/2014 |

OTHER PUBLICATIONS

Costa et al., (2010) "Guidelines to cell engineering for monoclonal antibody production," European J Pharmaceutics and Biopharmaceutics, 74:127-138.
(Continued)

*Primary Examiner* — Christian C Boesen
(74) *Attorney, Agent, or Firm* — Dechert LLP; Andrew T. Wilkins; Victoria E. Pedanou

(57) ABSTRACT

A triple expression vector is disclosed for expressing an antibody molecule comprising an Fc domain in prokaryotic cells and in eukaryotic cells. The triple expression vector comprises a polynucleotide encoding an Fc domain; a polynucleotide encoding a phage coat protein; a cloning site for cloning genes encoding an antibody molecule or a part thereof wherein the antibody molecule or part thereof does not comprise an Fc domain; a prokaryotic secretion signal sequence and a eukaryotic secretion signal sequence, or a secretion signal sequence that drives efficient secretion in both prokaryotic and eukaryotic cells; a promoter for mediating expression in eukaryotic cells; and a stop codon for preventing expression of the phage coat protein in eukaryotic cells. The triple expression vector can be used for
(Continued)

expressing an antibody molecule in a phage display format; for producing the antibody molecule in a prokaryotic cell, for example in the periplasm of a prokaryotic cell; and for producing the antibody molecule in a eukaryotic cell, for example a mammalian cell, more particularly a human cell. The antibody molecule contains an Fc domain, and may be for example a VHH-Fc molecule or an scFv-Fc molecule or a VH-Fc or a VL-Fc. Phage display libraries produced with the vector present the antibody molecule in its therapeutic format. Use of the vector avoids the need for repeated cloning when moving from one expression medium to another.

21 Claims, 20 Drawing Sheets

Specification includes a Sequence Listing.

(51) Int. Cl.
    *C12N 15/70*     (2006.01)
    *C12N 15/79*     (2006.01)
    *C07K 16/00*     (2006.01)
    *C12N 15/86*     (2006.01)

(52) U.S. Cl.
    CPC ............. *C12N 15/79* (2013.01); *C12N 15/86* (2013.01); *C07K 2317/52* (2013.01); *C07K 2317/524* (2013.01); *C07K 2317/526* (2013.01); *C07K 2317/53* (2013.01); *C07K 2317/569* (2013.01); *C12N 2830/00* (2013.01); *C12N 2840/00* (2013.01)

(56) References Cited

OTHER PUBLICATIONS

Frenzel et al., (2013) "Expression of recombinant antibodies," Frontiers in Immunology, 4(217):1-20.
Hmila et al., (2008) "VHH, bivalent domains and chimeric heavy chain-only antibodies with high neutralizing efficacy for scorpion toxin Aahl'," Molecular Immunology, 45:3847-3856.
International Search Report and Written Opinion for International Application No. PCT/EP2017/075983, dated Jan. 19, 2018.
Koerber et al., (2015) "An improved single-chain Fab platform for efficient display and recombinant expression," J. Mol. Biol., 427:576-586.
Kunert et al., (2016) "Advances in recombinant antibody manufacturing," Appl. Microbiol. Biotechnol., 100:3451-3461.
Robinson et al., (2015) "Efficient expression of full-length antibodies in the cytoplasm of engineered bacteria," Nature Communications, 6(27):1-9.
Smith et al., (2014) "Antibody library display on a mammalian virus vector: combining the advantages of both phage and yeast display into one technology," Current Drug Discovery Technologies, 11:48-55.
Tesar et al., (2013) "A dual host vector for Fab phage display and expression of native IgG in mammalian cells," Protein Eng. Des. Sel., 26(10):655-662.
Mazor et al., "Selection of full-length IgGs by tandem display on filamentous phage particles and *Escherichia coli* flourescence-activated cell sorting screening", The FEBS Journal, 2010, 277: 2291-2303.
Combined Search and Examination Report for Great Britain Application No. GB1617270.2, dated Aug. 3, 2017, 6 pages.
Shang et al., "Modular protein expression by RNA trans-splicing enables flexible expression of antibody formats in mammalian cells from a dual-host phage display vector", Protein Engineering, Design & Selection, 2015, vol. 28, No. 10, pp. 437-444.

Phage displayed VHH-Fc

Soluble VHH-Fc produced in bacteria

Fig. 4

| CDR3 AMINO ACID SEQUENCES | SEQ ID NOS | NUMBER OF ANTI-ABDEG | |
| --- | --- | --- | --- |
| | | VHH-Fc molecules with CDR3 sequence | VHH molecules with CDR3 sequence |
| AHRTSATYNGVEDYDY | 23 | 1 | 0 |
| DLRTYYGSHNY | 24 | 10 | 0 |
| DLRTYYGSRDY/ DLRTYYGSREY | 25 26 | 54 | 5 |
| FPFAP | 27 | 11 | 20 |
| IGGQFATREY | 28 | 24 | 0 |
| LNIDTMRNA | 29 | 1 | 0 |
| NPMPTGDDVSIHYRDYERYAY | 30 | 18 | 7 |
| RRDYILQTMAVMNELRNAKADV | 31 | 1 | 0 |
| RTRERFRSGGYYRLPNDYDN | 32 | 9 | 0 |
| RWAFTTTQTMAVMNELRNAKADV | 33 | 2 | 0 |
| VYSLSYSYTGTSLREYDY | 34 | 1 | 0 |
| YNEFSQARS | 35 | 4 | 0 |
| LGRKPDY | 36 | 0 | 37 |
| MRSITPDY | 37 | 0 | 23 |
| ARFYYGLESVVNTDY | 38 | 0 | 1 |
| Total | | 136 | 93 |

Soluble VHH-Fc produced from pDCL5 in bacterial periplasm

Soluble VHH-Fc produced from pDCL5 in bacterial periplasm

Soluble VHH-Fc produced from pDCL5 in bacterial periplasm: 7A11

Soluble VHH-Fc produced from pDCL5 in bacterial periplasm: 7G04

Fig. 9 continued
Soluble VHH-Fc produced from pDCL5 in bacterial periplasm: 7F04
HEK293T WT
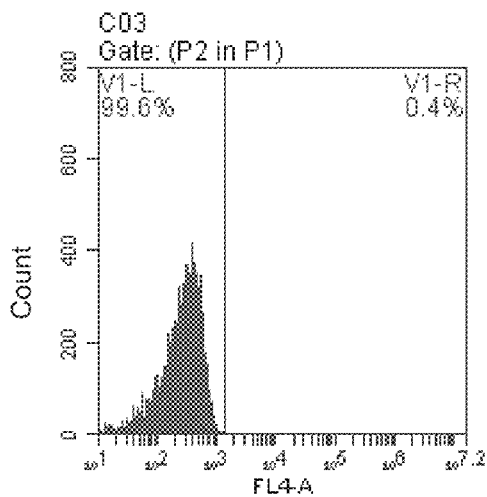
HEK293T-CXCR4
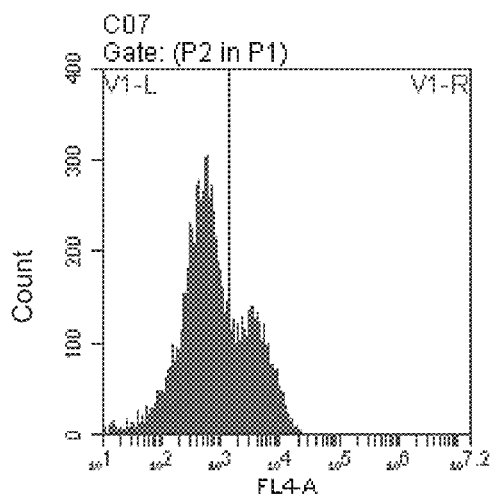
HEK293T-HER2
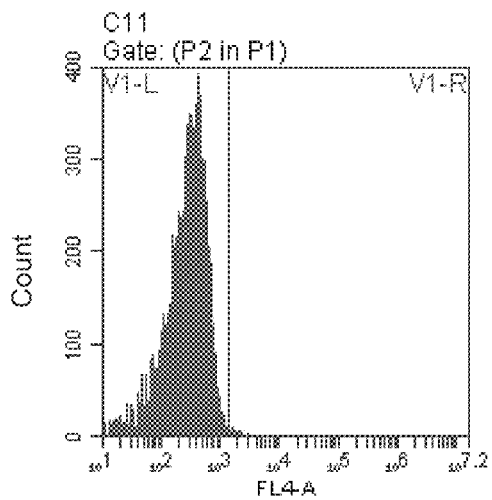

Soluble VHH-Fc produced from pDCL5 in bacterial periplasm: 7E10

Fig. 9 continued
Soluble VHH-Fc produced from pDCL5 in bacterial periplasm: 7B05
HEK293T WT
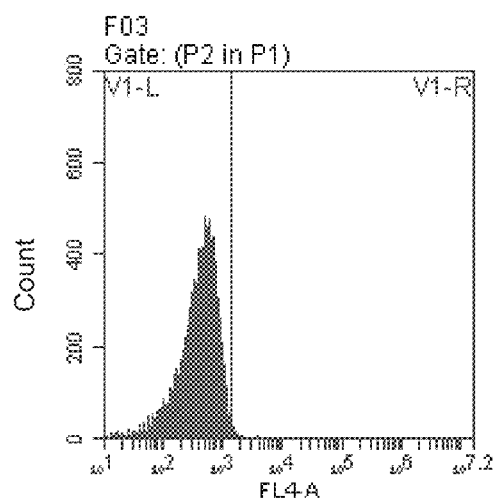
HEK293T-CXCR4
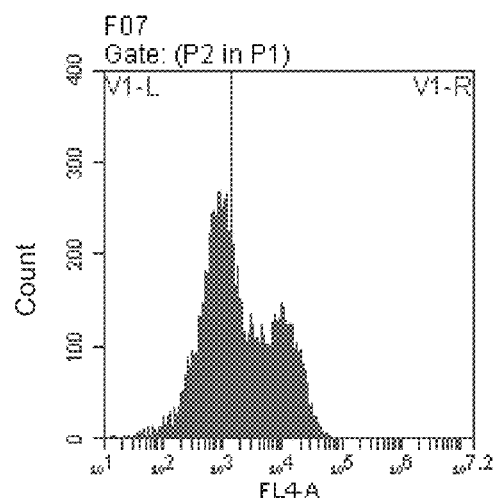
HEK293T-HER2
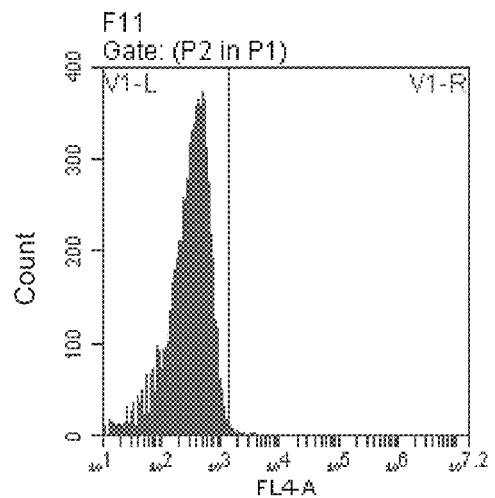

Fig. 9 continued
Soluble VHH-Fc produced from pDCL5 in bacterial periplasm: 3C04
HEK293T WT
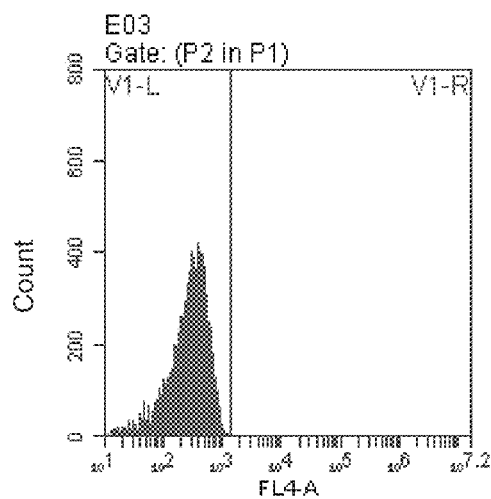
HEK293T-CXCR4
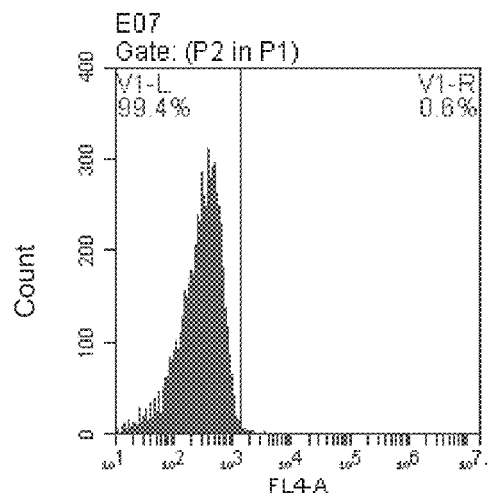
HEK293T-HER2
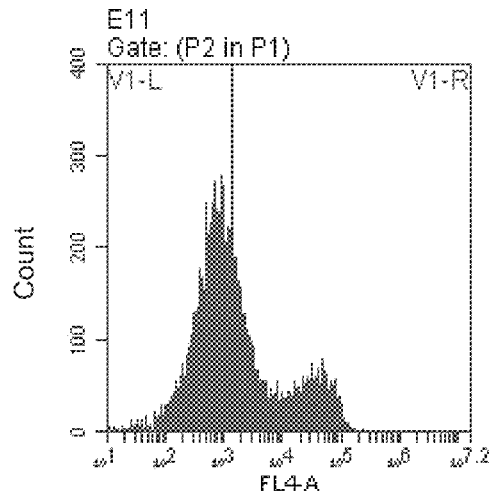

Fig. 11
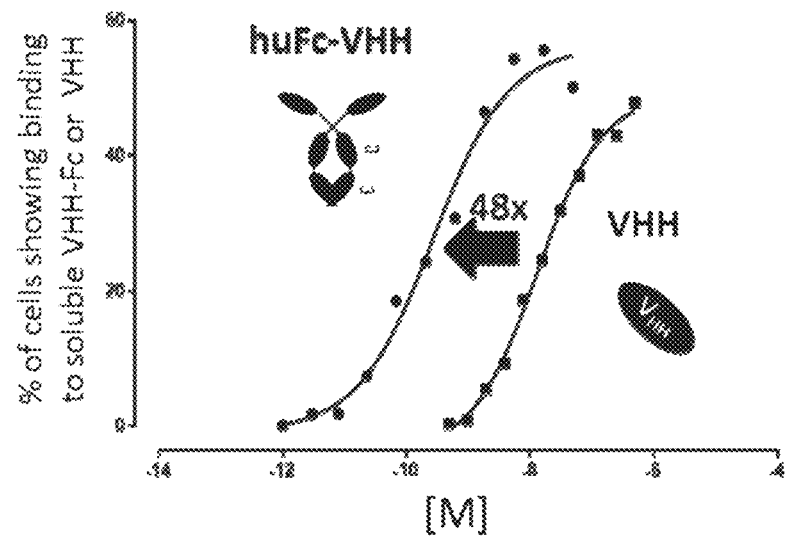
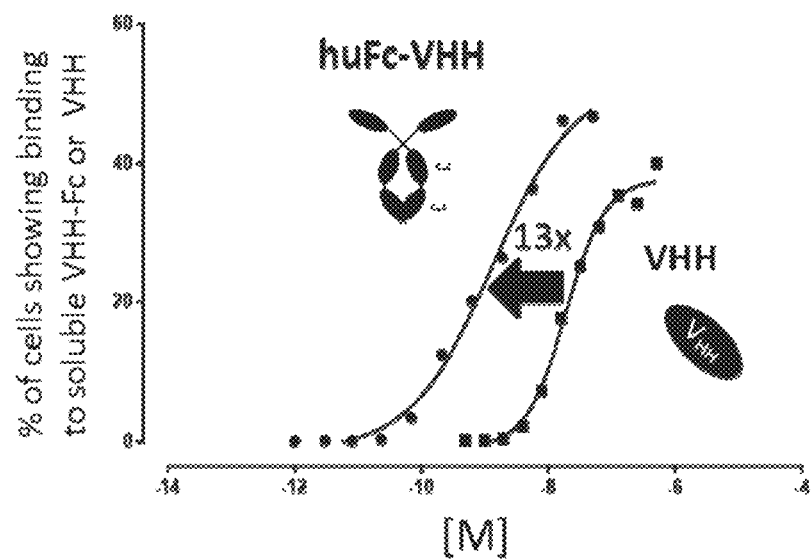

Fig.13

| CDR3 AMINO ACID SEQUENCES | SEQ ID NOS | NUMBER OF ANTI-HUMAN CDCR4 | |
|---|---|---|---|
| | | VHH-Fc molecules with CDR3 sequence | VHH molecules with CDR3 sequence |
| DREVSGSGSRWRGTFWDY | 39 | 1 | 0 |
| PLQRPWGSGDY | 40 | 3 | 2 |
| RVAGERLHRGRQYEFDY/ RVAGERLHRGRQYEYDY RVAGERLHRGRRYEYDY/ RVAGERLHRGRVYEYDY | 41 42 43 44 | 1 | 4 |
| RWGGSYHVSERDS | 45 | 0 | 1 |
| SLVGGSYSRGYDY | 46 | 0 | 1 |
| SPYSGSSRGYDY | 47 | 1 | 0 |
| VDGKQRGRGYDY | 48 | 1 | 0 |
| YRTGWGGRRGY | 49 | 0 | 2 |
| Total | | 7 | 10 |

SEQUENCE LISTING

<160> NUMBER OF SEQ ID NOS: 49

<210> SEQ ID NO 1
<211> LENGTH: 227
<212> TYPE: PRT
<213> ORGANISM: Homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 2
<211> LENGTH: 110
<212> TYPE: PRT
<213> ORGANISM: Homo sapiens

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 3
<211> LENGTH: 330
<212> TYPE: DNA
<213> ORGANISM: Homo sapiens

<400> SEQUENCE: 3
gccccggagc tcctgggcgg tccttccgtg ttcctctttc cgccaaagcc gaaagatacc      60
ttgatgatta gcagaacccc ggaggtgacg tgcgtcgtgg tcgacgtgtc ccacgaggat     120
ccggaagtca agttcaattg gtacgtcgac ggtgtggagg tgcacaacgc caagaccaag     180
ccgagagagg agcagtacaa ctccacctac cgcgtcgtga gcgtgctgac cgtgctgcac     240
caagactggt tgaacggcaa ggaatacaag tgcaaggtgt cgaacaaggc cctgccggcc     300
ccgatcgaaa agaccattag caaggcgaag                                      330

<210> SEQ ID NO 4
<211> LENGTH: 107
```

<212> TYPE: PRT
<213> ORGANISM: Homo sapiens

<400> SEQUENCE: 4

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 5
<211> LENGTH: 321
<212> TYPE: DNA
<213> ORGANISM: Homo sapiens

<400> SEQUENCE: 5
ggccagccgc gcgagccgca agtgtacacc ctcccgccat cacgggatga gctgaccaag      60
aaccaggtgt ccttgacgtg tctggtcaag ggcttctacc cgagcgacat tgccgtggag     120
tgggaatcca acggccagcc ggaaaacaac tataagacca ccccacctgt gcttgactcc     180
gatggttcct tcttcctgta ctccaagctg acggtggata gtcccgctg gcagcagggt      240 aacgtgttta gctgctcagt catgcacgaa gccctgcaca accactacac ccagaagtca     300
ctgtccctgt cgccaggcaa a                                                321

<210> SEQ ID NO 6
<211> LENGTH: 5262
<212> TYPE: DNA
<213> ORGANISM: Artificial
<220> FEATURE:
<223> OTHER INFORMATION: Vector

<400> SEQUENCE: 6
gcattaagcg cggcgggtgt ggtggttacg cgcagcgtga ccgctacact tgccagcgcc      60
ttagcgcccg ctcctttcgc tttcttccct cctttctcg ccacgttcgc cggctttccc      120
cgtcaagctc taaatcgggg gctcccttta gggttccgat ttagtgcttt acggcacctc     180
gaccccaaaa aacttgattt gggtgatggt tcacgtagtg ggccatcgcc ctgatagacg     240
gtttttcgcc ctttgacgtt ggagtccacg ttctttaata gtggactctt gttccaaact     300
ggaacaacac tcaactctat ctcgggctat tcttttgatt tataagggat tttgccgatt     360
tcggtctatt ggttaaaaaa tgagctgatt taacaaaaat ttaacgcgaa ttttaacaaa     420
atattaacgt ttacaatttt atggtgcagt ctcagtacaa tctgctctga tgccgcatag     480
ttaagccagc cccgacaccc gccaacaccc gctgacgcgc cctgacgggc ttgtctgctc     540
ccggcatccg cttacagaca agctgtgacc gtctccggga gctgcatgtg tcagaggttt     600
tcaccgtcat caccgaaacg cgcgagacga aagggcctcg tgatacgcct atttttatag     660
gttaatgtca tgataataat ggtttcttag acgtcaggtg gcacttttcg gggaaatgtg     720

```
cgcggaaccc ctatttgttt attttttctaa atacattcaa atatgtatcc gctcatgaga    780
caataaccct gataaatgct tcaataatat tgaaaaagga agagtatgag tattcaacat    840
ttccgtgtcg cccttattcc cttttttgcg gcattttgcc ttcctgtttt tgctcaccca    900
gaaacgctgg tgaaagtaaa agatgctgaa gatcagttgg gtgcccgagt gggttacatc    960
gaactggatc tcaacagcgg taagatcctt gagagttttc gccccgaaga acgttttcca   1020
atgatgagca cttttaaagt tctgctatgt ggcgcggtat tatcccgtat tgacgccggg   1080
caagagcaac tcggtcgccg catacactat tctcagaatg acttggttga gtactcacca   1140
gtcacagaaa agcatcttac ggatggcatg acagtaagag aattatgcag tgctgccata   1200
accatgagtg ataacactgc ggccaactta cttctgacaa cgatcggagg accgaaggag   1260
ctaaccgctt ttttgcacaa catgggggat catgtaactc gccttgatcg ttgggaaccg   1320
gagctgaatg aagccatacc aaacgacgag cgtgacacca cgatgcctgt agcaatggca   1380
acaacgttgc gcaaactatt aactggcgaa ctacttactc tagcttcccg gcaacaatta   1440
atagactgga tggaggcgga taaagttgca ggaccacttc tgcgctcggc ccttccggct   1500
ggctggttta ttgctgataa atctggagcc ggtgagcgtg ggtctcgcgg tatcattgca   1560
gcactggggc cagatggtaa gccctcccgt atcgtagtta tctacacgac ggggagtcag   1620
gcaactatgg atgaacgaaa tagacagatc gctgagatag gtgcctcact gattaagcat   1680
tggtaactgt cagaccaagt ttactcatat atactttaga ttgatttaaa acttcatttt   1740
taatttaaaa ggatctaggt gaagatcctt tttgataatc tcatgaccaa aatcccttaa   1800
cgtgagtttt cgttccactg agcgtcagac cccgtagaaa agatcaaagg atcttcttga   1860 gatcctttt ttctgcgcgt aatctgctgc ttgcaaacaa aaaaaccacc gctaccagcg   1920
gtggtttgtt tgccggatca agagctacca actctttttc cgaaggtaac tggcttcagc   1980
agagcgcaga taccaaatac tgttcttcta gtgtagccgt agttaggcca ccacttcaag   2040
aactctgtag caccgcctac atacctcgct ctgctaatcc tgttaccagt ggctgctgcc   2100
agtggcgata agtcgtgtct taccgggttg gactcaagac gatagttacc ggataaggcg   2160
cagcggtcgg gctgaacggg gggttcgtgc atacagccca gcttggagcg aacgacctac   2220
accgaactga gatacctaca gcgtgagcta tgagaaagcg ccacgcttcc cgaagggaga   2280
aaggcggaca ggtatccggt aagcggcagg gtcggaacag gagagcgcac gagggagctt   2340
ccagggggaa acgcctggta tctttatagt cctgtcgggt ttcgccacct ctgacttgag   2400
cgtcgatttt tgtgatgctc gtcagggggg cggagcctat ggaaaaacgc cagcaacgcg   2460
gcctttttac ggttcctggc cttttgctgg ccttttgctc acatgttctt tcctgcgtta   2520
tcccctgatt ctgtggataa ccgtattacc gcctttgagt gagctgatac cgctcgccgc   2580
agccgaacga ccgagcgcag cgagtcagtg agcgaggaag cggaagagcg cccaatacgc   2640
aaaccgcctc tccccgcgcg ttggccgatt cattaatgca gctggcacga caggtttccc   2700
gactggaaag cgggcagtga gcgcaacgca attaatgtga gttagctcac tcattaggca   2760
ccccaggctt tacactttat gcttccggct cgtatgttgt gtggaattgt gagcggataa   2820
caatttcaca caggaaacag ctatgaccat gattacgcca agcttgcatg caaattctat   2880
ttcaaggaga cagtcataat gaaataccta ttgcctacgg cagccgctgg attgttatta   2940
ctcgcggccc agccggccat ggcccaggtg cagctgcagg agtcataatg agggacccag   3000
gtcaccgtct caagcgacaa gacacacacc tgccctcctt gtccagcccc cgaactgctg   3060
```

```
ggtgggccca gcgtgttcct gtttcctcct aaacccaaag acactctgat gattagtagg    3120
accccagaag tcacttgcgt ggtggttgac gtgtcacatg aagatcccga ggtcaagttc    3180
aattggtatg ttgacggggt cgaagttcac aacgctaaaa ctaaaccaag agaggaacag    3240
tataactcta cctaccgggt ggtgagtgtt ctgactgtcc tccatcaaga ctggctgaat    3300
ggcaaagaat acaagtgtaa ggtgagcaac aaagccctgc ccgctcctat agagaaaaca    3360
atatccaaag ccaaaggtca acctcgcgag ccacaggtgt acaccctccc accaagccgc    3420
gatgaactta ctaagaacca gtctctcttt acttgcctgg ttaaggggtt ctatccatcc    3480
gacattgcag tcgagtggga gtctaatgga cagcctgaga acaactacaa aaccacccct    3540
cctgttctgg attctgacgg atctttcttc ctttattcta aactcaccgt ggataaaagc    3600
aggtggcagc agggcaacgt gttcagctgt tccgttatgc atgaggccct gcataaccat    3660
tatacccaga agtctttgtc cctcagtcca ggaaaggcgg ccgcacatca tcatcaccat    3720
cacggggccg cagaacaaaa actcatctca gaagaggatc tgaatggggc cgcatagact    3780
gttgaaagtt gtttagcaaa acctcataca gaaaattcat ttactaacgt ctggaaagac    3840
gacaaaactt tagatcgtta cgctaactat gagggctgtc tgtggaatgc tacaggcgtt    3900
gtggtttgta ctggtgacga aactcagtgt tacggtacat gggttcctat tgggcttgct    3960
atccctgaaa atgagggtgg tggctctgag ggtggcggtt ctgagggtgg cggttctgag    4020
ggtggcggta ctaaacctcc tgagtacggt gatacaccta ttccgggcta tacttatatc    4080
aaccctctcg acggcactta tccgcctggt actgagcaaa accccgctaa tcctaatcct    4140
tctcttgagg agtctcagcc tcttaatact ttcatgtttc agaataatag gttccgaaat    4200
aggcagggtg cattaactgt ttatacgggc actgttactc aaggcactga ccccgttaaa    4260
acttattacc agtacactcc tgtatcatca aaagccatgt atgacgctta ctggaacggt    4320
aaattcagag actgcgcttt ccattctggc tttaatgagg atccattcgt ttgtgaatat    4380
caaggccaat cgtctgacct gcctcaacct cctgtcaatg ctggcggcgg ctctggtggt    4440
ggttctggtg gcggctctga gggtggcggc tctgagggtg gcggctctga gggtggcggt    4500
tctgagggtg gcggctctga gggtggcggt tccggtggcg gctccggttc cggtgatttt    4560
gattatgaaa aaatggcaaa cgctaataag ggggctatga ccgaaaatgc cgatgaaaac    4620
gcgctacagt ctgacgctaa aggcaaactt gattctgtcg ctactgatta cggtgctgct    4680
atcgatggtt tcattggtga cgtttccggc cttgctaatg gtaatggtgc tactggtgat    4740
tttgctggct ctaattccca aatggctcaa gtcggtgacg gtgataattc acctttaatg    4800
aataatttcc gtcaatattt accttctttg cctcagtcgg ttgaatgtcg cccttatgtc    4860
tttggcgctg gtaaaccata tgaattttct attgattgtg acaaaataaa cttattccgt    4920
ggtgtctttg cgtttctttt atatgttgcc acctttatgt atgtattttc gacgtttgct    4980
aacatactgc gtaataagga gtcttaataa gaattcactg gccgtcgttt tacaacgtcg    5040
tgactgggaa aaccctggcg ttacccaact taatcgcctt gcagcacatc cccctttcgc    5100
cagctggcgt aatagcgaag aggcccgcac cgatcgccct tcccaacagt tgcgcagcct    5160
gaatggcgaa tggcgcctga tgcggtattt tctccttacg catctgtgcg gtatttcaca    5220
ccgcatacgt caaagcaacc atagtacgcg ccctgtagcg gc                      5262
```

<210> SEQ ID NO 7
<211> LENGTH: 6652
<212> TYPE: DNA
<213> ORGANISM: Artificial

<220> FEATURE:
<223> OTHER INFORMATION: Vector

<400> SEQUENCE: 7

```
gagtgagctg ataccgctcg ccgcagccga acgaccgagc gcagcgagtc agtgagcgag      60
gaagcggaaa acgcccaat acgcaaaccg cctcttcccc gcgcgttggc cgattcatta     120
atgcagcgtc gacactgcgg gggctctgga gacgacttac ggtaaatggc ccgcctggct     180
gaccgcccaa cgaccccgc ccattgacgt caataatgac gtatgttccc atagtaacgc     240
caatagggac tttccattga cgtcaatggg tggagtattt acggtaaact gcccacttgg     300
cagtacatca agtgtatcat atgccaagtc cgcccctat tgacgtcaat gacggtaaat     360
ggcccgcctg gcattatgcc cagtacatga ccttacggga ctttcctact tggcagtaca     420
tctacgtatt agtcatcgct attaccatgc tgatgcggtt ttggcagtac accaatgggc     480
gtggatagcg gtttgactca cggggatttc caagtctcca ccccattgac gtcaatggga     540
gtttgttttg gcaccaaaat caacgggact ttccaaaatg tcgtaataac cccgccccgt     600
tgacgcaaat gggcggtagg cgtgtacggt gggaggtcta tataagcaga gctcgtttag     660
tgaaccgtca gatcgcctgg agaggccatc cacgctgttt tgacctccat agtggacacc     720
gggaccgatc cagcctccgc ggccgggaac ggtgcattgg aacgcggatt ccccgtgcca     780
agagtgaccc tggcagaact cggtaagtct gttgacatgt atgtgatgta tactaacctg     840
catgggacgt ggatttactt gtgtatgtca gatagagtaa agattaactc ttgcatgtga     900
gcggggcatc gagatagcga taatgagtc aggaggacgg atacttatat gtgttgttat     960
cctcctctac agtcaaacag attaagcgtc tcaggggtgg cacgacaggt ttcccgactg    1020
gaaagcgggc agtgagcgca acgcaattaa tgtgagttag ctcactcatt aggcacccca    1080
ggctttacac tttatgcttc cggctcgtat gttgtgtgga attgtgagcg ataacaatt    1140
acggtttccc tctagaaata attttgttta acaggaggtg ccaccatgat gaaatttact    1200
gtcgtcgctg ctgcgttgtt gttgttgggt gcagtgcgcg caatgtaagt aactaactag    1260
ctgtgtgaga acaggctacg aaatcccctg tggatgactg gcaagtcgtt gttggccacc    1320
aatcttacac caccgttata gtcggacgcc tgtagtgcaa gtgcaccgcg cgatggtcct    1380
tacgggttac tgacgccatt ctgtcctccc atctgatcta tgcgaaaccg cctcatcgtg    1440
caggtcaccg tctcctcaga caagacccac acgtgcccgc cgtgcccggc cccggagctc    1500
ctgggcggtc cttccgtgtt cctctttccg ccaaagccga aagataccct tgatgattagc   1560
agaaccccgg aggtgacgtg cgtcgtggtc gacgtgtccc acgaggatcc ggaagtcaag    1620
ttcaattggt acgtcgacgg tgtggaggtg cacaacgcca agaccaagcc gagagaggag    1680
cagtacaact ccacctaccg cgtcgtgagc gtgctgaccg tgctgcacca agactggttg    1740
aacggcaagg aatacaagtg caaggtgtcg aacaaggccc tgccggcccc gatcgaaaag    1800
accattagca aggcgaaggg ccagccgcgc gagccgcaag tgtacaccct cccgccatca    1860
cgggatgagc tgaccaagaa ccaggtgtcc ttgacgtgtc tggtcaaggg cttctacccg    1920
agcgacattg ccgtggagtg ggaatccaac ggccagccgg aaaacaacta taagaccacc    1980
ccacctgtgc ttgactccga tggttccttc ttcctgtact ccaagctgac ggtggataag    2040
tcccgctggc agcagggtaa cgtgtttagc tgctcagtca tgcacgaagc cctgcacaac    2100
cactacaccc agaagtcact gtccctgtcg ccaggcaaag cggcggcgca tcatcatcac    2160
catcacgggg ccgcagaaca aaaactcatc tcagaagagg atctgaatgg ggccgcatag    2220
```

```
actgttgaaa gttgtttagc aaaacctcat acagaaaatt catttactaa cgtctggaaa    2280
gacgacaaaa cttttagatcg ttacgctaac tatgagggct gtctgtggaa tgctacaggc   2340
gttgtggttt gtactggtga cgaaactcag tgttacggta catgggttcc tattgggctt    2400
gctatccctg aaaatgaggg tggtggctct gagggtggcg gttctgaggg tggcggttct    2460
gagggtggcg gtactaaacc tcctgagtac ggtgatacac ctattccggg ctatacttat    2520
atcaaccctc tcgacggcac ttatccgcct ggtactgagc aaaacccccgc taatcctaat    2580 ccttctcttg aggagtctca gcctcttaat actttcatgt ttcagaataa taggttccga   2640
aataggcagg gtgcattaac tgtttatacg ggcactgtta ctcaaggcac tgaccccgtt    2700
aaaacttatt accagtacac tcctgtatca tcaaaagcca tgtatgacgc ttactggaac    2760
ggtaaattca gagactgcgc tttccattct ggctttaatg aggatccatt cgtttgtgaa   2820
tatcaaggcc aatcgtctga cctgcctcaa cctcctgtca atgctggcgg cggctctggt   2880
ggtggttctg gtggcggctc tgagggtggc ggctctgagg gtggcggctc tgagggtggc   2940
ggttctgagg gtggcggctc tgagggtggc ggttccggtg cgggctccgg ttccggtgat   3000
tttgattatg aaaaaatggc aaacgctaat aaggggggcta tgaccgaaaa tgccgatgaa    3060
aacgcgctac agtctgacgc taaaggcaaa cttgattctg tcgctactga ttacggtgct   3120
gctatcgatg gtttcattgg tgacgtttcc ggccttgcta atggtaatgg tgctactggt   3180
gattttgctg gctctaattc ccaaatggct caagtcggtg acggtgataa ttcaccttta   3240
atgaataatt tccgtcaata tttaccttct ttgcctcagt cggttgaatg tcgcccttat    3300
gtctttggcg ctggtaaacc atatgaattt tctattgatt gtgacaaaat aaacttattc   3360
cgtggtgtct ttgcgtttct tttatatgtt gccaccttta tgtatgtatt ttcgacgttt    3420
gctaacatac tgcgtaataa ggagtcttaa taaaaaatgg ctaataaagg aaatttattt   3480
tcattgcaat agtgtgttgg aattttttgt gtctctcact cggaaggaca tatgggaggg   3540
caaatcattt aaaacatcag aatgagtatt tggtttagag tttggcaaca tatgcccata   3600
tgctggctgc catgaacaaa ggttggctat aaagaggtca tcagtatatg aaacagcccc   3660
ctgctgtcca ttccttattc catagaaaag ccttgacttg aggttagatt tttttttatat   3720 tttgttttgt gttattttttt tctttaacat ccctaaaatt ttccttacat gttttactag   3780
ccagattttt cctcctctcc tgactactcc cagtcatagc tgtccctctt ctcttatgga   3840
gatcgaattc actggccgtc gttttacaac gtcgtgactg ggaaaaccct ggcgttaccc   3900
aacttaatcg ccttgcagca catccccctt tcgccagctg gcgtaatagc gaagaggccc   3960
gcaccgatcg cccttcccaa cagttgcgca gcctgaatgg cgaatggcgc ctgatgcggt   4020
attttctcct tacgcatctg tgcggtattt cacaccgcat acgtcaaagc aaccatagta   4080
cgcgccctgt agcggcgcat taagcgcggc gggtgtggtg gttacgcgca gcgtgaccgc   4140
tacacttgcc agcgccttag cgcccgctcc tttcgctttc ttcccttcct ttctcgccac   4200
gttcgccggc tttccccgtc aagctctaaa tcggggggctc cctttagggt tccgatttag   4260
tgctttacgg cacctcgacc ccaaaaaact tgatttgggt gatggttcac gtagtgggcc   4320
atcgccctga tagacggttt ttcgcccttt gacgttggag tccacgttct ttaatagtgg   4380
actcttgttc caaactggaa caacactcaa ctctatctcg gctattcttt tgatttata    4440 agggattttg ccgatttcgg tctattggtt aaaaaatgag ctgatttaac aaaaatttaa   4500
cgcgaatttt aacaaaatat taacgtttac aattttatgg tgcagtctca gtacaatctg   4560
ctctgatgcc gcatagttaa gccagccccg acacccgcca cacccgctg acgcgccctg    4620
```

```
acgggcttgt ctgctcccgg catccgctta cagacaagct gtgaccgtct ccgggagctg    4680
catgtgtcag aggttttcac cgtcatcacc gaaacgcgcg agacgaaagg gcctcgtgat    4740
acgcctattt ttataggtta atgtcatgat aataatggtt tcttagacgt caggtggcac    4800
ttttcgggga aatgtgcgcg gaaccccgat ttgtttattt ttctaaatac attcaaatat    4860
gtatccgctc atgagacaat aaccctgata aatgcttcaa taatattgaa aaaggaagag    4920
tatgagtatt caacatttcc gtgtcgccct tattccctt tttgcggcat tttgccttcc     4980 tgttttgct cacccagaaa cgctggtgaa agtaaaagat gctgaagatc agttgggtgc    5040
ccgagtgggt tacatcgaac tggatctcaa cagcggtaag atccttgaga gttttcgccc    5100
cgaagaacgt tttccaatga tgagcacttt taaagttctg ctatgtggcg cggtattatc    5160
ccgtattgac gccgggcaag agcaactcgg tcgccgcata cactattctc agaatgactt    5220
ggttgagtac tcaccagtca cagaaaagca tcttacggat ggcatgacag taagagaatt    5280
atgcagtgct gccataacca tgagtgataa cactgcggcc aacttacttc tgacaacgat    5340
cggaggaccg aaggagctaa ccgcttttt gcacaacatg ggggatcatg taactcgcct     5400
tgatcgttgg gaaccggagc tgaatgaagc cataccaaac gacgagcgtg acaccacgat    5460
gcctgtagca atggcaacaa cgttgcgcaa actattaact ggcgaactac ttactctagc    5520
ttcccggcaa caattaatag actggatgga ggcggataaa gttgcaggac cacttctgcg    5580
ctcggccctt ccggctggct ggtttattgc tgataaatct ggagccggtg agcgtgggtc    5640
tcgcggtatc attgcagcac tggggccaga tggtaagccc tcccgtatcg tagttatcta    5700
cacgacgggg agtcaggcaa ctatggatga acgaaataga cagatcgctg agataggtgc    5760
ctcactgatt aagcattggt aactgtcaga ccaagtttac tcatatatac tttagattga    5820
tttaaaactt cattttaat ttaaaaggat ctaggtgaag atccttttg ataatctcat       5880 gaccaaaatc ccttaacgtg agttttcgtt ccactgagcg tcagaccccg tagaaaagat    5940
caaaggatct tcttgagatc cttttttct gcgcgtaatc tgctgcttgc aaacaaaaaa     6000
accaccgcta ccagcggtgg tttgtttgcc ggatcaagag ctaccaactc tttttccgaa    6060
ggtaactggc ttcagcagag cgcagatacc aaatactgtt cttctagtgt agccgtagtt    6120
aggccaccac ttcaagaact ctgtagcacc gcctacatac ctcgctctgc taatcctgtt    6180
accagtggct gctgccagtg gcgataagtc gtgtcttacc gggttggact caagacgata    6240
gttaccggat aaggcgcagc ggtcgggctg aacggggggt tcgtgcatac agcccagctt    6300
ggagcgaacg acctacaccg aactgagata cctacagcgt gagctatgag aaagcgccac    6360
gcttcccgaa gggagaaagg cggacaggta tccggtaagc ggcagggtcg gaacaggaga    6420
gcgcacgagg gagcttccag ggggaaacgc ctggtatctt tatagtcctg tcgggtttcg    6480
ccacctctga cttgagcgtc gatttttgtg atgctcgtca ggggggcgga gcctatggaa    6540
aaacgccagc aacgcggcct ttttacggtt cctggccttt tgctggcctt ttgctcacat    6600
gttctttcct gcgttatccc ctgattctgt ggataaccgt attaccgcct tt            6652
```

<210> SEQ ID NO 8
<211> LENGTH: 10
<212> TYPE: PRT
<213> ORGANISM: Homo sapiens

<400> SEQUENCE: 8

Asp Lys Thr His Thr Cys Pro Pro Cys Pro
1               5                   10

<210> SEQ ID NO 9
<211> LENGTH: 30
<212> TYPE: DNA
<213> ORGANISM: Homo sapiens

<400> SEQUENCE: 9
gacaagaccc acacgtgccc gccgtgcccg                                    30

<210> SEQ ID NO 10
<211> LENGTH: 19
<212> TYPE: PRT
<213> ORGANISM: Homo sapiens

<400> SEQUENCE: 10

Met Gly Trp Ser Cys Ile Ile Leu Phe Leu Val Ala Thr Ala Thr Gly
1               5                   10                  15

Val His Ser

<210> SEQ ID NO 11
<211> LENGTH: 10
<212> TYPE: PRT
<213> ORGANISM: Homo sapiens

<400> SEQUENCE: 11

Glu Pro Lys Ser Cys Asp Lys Thr His Thr
1               5                   10

<210> SEQ ID NO 12
<211> LENGTH: 5
<212> TYPE: PRT
<213> ORGANISM: Homo sapiens

<400> SEQUENCE: 12

Cys Pro Pro Cys Pro
1               5

<210> SEQ ID NO 13
<211> LENGTH: 8
<212> TYPE: PRT
<213> ORGANISM: Homo sapiens

<400> SEQUENCE: 13

Ala Pro Glu Leu Leu Gly Gly Pro
1               5

<210> SEQ ID NO 14
<211> LENGTH: 12
<212> TYPE: PRT
<213> ORGANISM: Homo sapiens

<400> SEQUENCE: 14

Glu Leu Lys Thr Pro Leu Gly Asp Thr Thr His Thr
1               5                   10

<210> SEQ ID NO 15
<211> LENGTH: 50
<212> TYPE: PRT
<213> ORGANISM: Homo sapiens

<400> SEQUENCE: 15

Cys Pro Arg Cys Pro Glu Pro Lys Ser Cys Asp Thr Pro Pro Pro Cys
1               5                   10                  15

```
Pro Arg Cys Pro Glu Pro Lys Ser Cys Asp Thr Pro Pro Cys Pro
            20                  25                  30

Arg Cys Pro Glu Pro Lys Ser Cys Asp Thr Pro Pro Cys Pro Arg
        35                  40                  45

Cys Pro
    50

<210> SEQ ID NO 16
<211> LENGTH: 8
<212> TYPE: PRT
<213> ORGANISM: Homo sapiens

<400> SEQUENCE: 16

Ala Pro Glu Leu Leu Gly Gly Pro
1               5

<210> SEQ ID NO 17
<211> LENGTH: 7
<212> TYPE: PRT
<213> ORGANISM: Homo sapiens

<400> SEQUENCE: 17

Glu Ser Lys Tyr Gly Pro Pro
1               5

<210> SEQ ID NO 18
<211> LENGTH: 5
<212> TYPE: PRT
<213> ORGANISM: Homo sapiens

<400> SEQUENCE: 18

Cys Pro Ser Cys Pro
1               5

<210> SEQ ID NO 19
<211> LENGTH: 8
<212> TYPE: PRT
<213> ORGANISM: Homo sapiens

<400> SEQUENCE: 19

Ala Pro Glu Phe Leu Gly Gly Pro
1               5

<210> SEQ ID NO 20
<211> LENGTH: 3
<212> TYPE: PRT
<213> ORGANISM: Homo sapiens

<400> SEQUENCE: 20

Glu Arg Lys
1

<210> SEQ ID NO 21
<211> LENGTH: 10
<212> TYPE: PRT
<213> ORGANISM: Homo sapiens

<400> SEQUENCE: 21

Cys Cys Val Glu Cys Pro Pro Cys Pro
1               5                   10

<210> SEQ ID NO 22
<211> LENGTH: 7
<212> TYPE: PRT
```

-continued

<213> ORGANISM: Homo sapiens

<400> SEQUENCE: 22

Ala Pro Pro Val Ala Gly Pro
1               5

<210> SEQ ID NO 23
<211> LENGTH: 16
<212> TYPE: PRT
<213> ORGANISM: Llama paca

<400> SEQUENCE: 23

Ala His Arg Thr Ser Ala Thr Tyr Asn Gly Val Glu Asp Tyr Asp Tyr
1               5                   10                  15

<210> SEQ ID NO 24
<211> LENGTH: 11
<212> TYPE: PRT
<213> ORGANISM: Llama paca

<400> SEQUENCE: 24

Asp Leu Arg Thr Tyr Tyr Gly Ser His Asn Tyr
1               5                   10

<210> SEQ ID NO 25
<211> LENGTH: 11
<212> TYPE: PRT
<213> ORGANISM: Llama paca

<400> SEQUENCE: 25

Asp Leu Arg Thr Tyr Tyr Gly Ser Arg Asp Tyr
1               5                   10

<210> SEQ ID NO 26
<211> LENGTH: 11
<212> TYPE: PRT
<213> ORGANISM: Llama paca

<400> SEQUENCE: 26

Asp Leu Arg Thr Tyr Tyr Gly Ser Arg Glu Tyr
1               5                   10

<210> SEQ ID NO 27
<211> LENGTH: 5
<212> TYPE: PRT
<213> ORGANISM: Llama paca

<400> SEQUENCE: 27

Phe Pro Phe Ala Pro
1               5

<210> SEQ ID NO 28
<211> LENGTH: 10
<212> TYPE: PRT
<213> ORGANISM: Llama paca

<400> SEQUENCE: 28

Ile Gly Gly Gln Phe Ala Thr Arg Glu Tyr
1               5                   10

<210> SEQ ID NO 29
<211> LENGTH: 9
<212> TYPE: PRT
<213> ORGANISM: Llama paca

```
<400> SEQUENCE: 29

Leu Asn Ile Asp Thr Met Arg Asn Ala
1               5

<210> SEQ ID NO 30
<211> LENGTH: 21
<212> TYPE: PRT
<213> ORGANISM: Llama paca

<400> SEQUENCE: 30

Asn Pro Met Pro Thr Gly Asp Asp Val Ser Ile His Tyr Arg Asp Tyr
1               5                   10                  15

Glu Arg Tyr Ala Tyr
            20

<210> SEQ ID NO 31
<211> LENGTH: 15
<212> TYPE: PRT
<213> ORGANISM: Llama paca

<400> SEQUENCE: 31

Arg Arg Asp Tyr Ile Leu Gln Thr Asn Ala Asp Asp Tyr Asp Phe
1               5                   10                  15

<210> SEQ ID NO 32
<211> LENGTH: 20
<212> TYPE: PRT
<213> ORGANISM: Llama paca

<400> SEQUENCE: 32

Arg Thr Arg Glu Arg Phe Arg Ser Gly Gly Tyr Tyr Arg Leu Pro Asn
1               5                   10                  15

Asp Tyr Asp Asn
            20

<210> SEQ ID NO 33
<211> LENGTH: 23
<212> TYPE: PRT
<213> ORGANISM: Llama paca

<400> SEQUENCE: 33

Arg Trp Ala Phe Thr Thr Thr Gln Thr Met Ala Val Met Asn Glu Leu
1               5                   10                  15

Arg Asn Ala Lys Ala Asp Val
            20

<210> SEQ ID NO 34
<211> LENGTH: 18
<212> TYPE: PRT
<213> ORGANISM: Llama paca

<400> SEQUENCE: 34

Val Tyr Ser Leu Ser Tyr Ser Tyr Thr Gly Thr Ser Leu Arg Glu Tyr
1               5                   10                  15

Asp Tyr

<210> SEQ ID NO 35
<211> LENGTH: 9
<212> TYPE: PRT
<213> ORGANISM: Llama paca

<400> SEQUENCE: 35
```

Tyr Asn Glu Phe Ser Gln Ala Arg Ser
1               5

<210> SEQ ID NO 36
<211> LENGTH: 7
<212> TYPE: PRT
<213> ORGANISM: Llama paca

<400> SEQUENCE: 36

Leu Gly Arg Lys Pro Asp Tyr
1               5

<210> SEQ ID NO 37
<211> LENGTH: 8
<212> TYPE: PRT
<213> ORGANISM: Llama paca

<400> SEQUENCE: 37

Met Arg Ser Ile Thr Pro Asp Tyr
1               5

<210> SEQ ID NO 38
<211> LENGTH: 15
<212> TYPE: PRT
<213> ORGANISM: Llama paca

<400> SEQUENCE: 38

Ala Arg Phe Tyr Tyr Gly Leu Glu Ser Val Val Asn Thr Asp Tyr
1               5                   10                  15

<210> SEQ ID NO 39
<211> LENGTH: 18
<212> TYPE: PRT
<213> ORGANISM: Llama paca

<400> SEQUENCE: 39

Asp Arg Glu Val Ser Gly Ser Gly Ser Arg Trp Arg Gly Thr Phe Trp
1               5                   10                  15

Asp Tyr

<210> SEQ ID NO 40
<211> LENGTH: 11
<212> TYPE: PRT
<213> ORGANISM: Llama paca

<400> SEQUENCE: 40

Pro Leu Gln Arg Pro Trp Gly Ser Gly Asp Tyr
1               5                   10

<210> SEQ ID NO 41
<211> LENGTH: 17
<212> TYPE: PRT
<213> ORGANISM: Llama paca

<400> SEQUENCE: 41

Arg Val Ala Gly Glu Arg Leu His Arg Gly Arg Gln Tyr Glu Phe Asp
1               5                   10                  15

Tyr

<210> SEQ ID NO 42
<211> LENGTH: 17
<212> TYPE: PRT
<213> ORGANISM: Llama paca

-continued

<400> SEQUENCE: 42

Arg Val Ala Gly Glu Arg Leu His Arg Gly Arg Gln Tyr Glu Tyr Asp
1               5                   10                  15
Tyr

<210> SEQ ID NO 43
<211> LENGTH: 17
<212> TYPE: PRT
<213> ORGANISM: Llama paca

<400> SEQUENCE: 43

Arg Val Ala Gly Glu Arg Leu His Arg Gly Arg Arg Tyr Glu Tyr Asp
1               5                   10                  15
Tyr

<210> SEQ ID NO 44
<211> LENGTH: 17
<212> TYPE: PRT
<213> ORGANISM: Llama paca

<400> SEQUENCE: 44

Arg Val Ala Gly Glu Arg Leu His Arg Gly Arg Val Tyr Glu Tyr Asp
1               5                   10                  15
Tyr

<210> SEQ ID NO 45
<211> LENGTH: 13
<212> TYPE: PRT
<213> ORGANISM: Llama paca

<400> SEQUENCE: 45

Arg Trp Gly Gly Ser Tyr His Val Ser Glu Arg Asp Ser
1               5                   10

<210> SEQ ID NO 46
<211> LENGTH: 13
<212> TYPE: PRT
<213> ORGANISM: Llama paca

<400> SEQUENCE: 46

Ser Leu Val Gly Gly Ser Tyr Ser Arg Gly Tyr Asp Tyr
1               5                   10

<210> SEQ ID NO 47
<211> LENGTH: 12
<212> TYPE: PRT
<213> ORGANISM: Llama paca

<400> SEQUENCE: 47

Ser Pro Tyr Ser Gly Ser Ser Arg Gly Tyr Asp Tyr
1               5                   10

<210> SEQ ID NO 48
<211> LENGTH: 12
<212> TYPE: PRT
<213> ORGANISM: Llama paca

<400> SEQUENCE: 48

Val Asp Gly Lys Gln Arg Gly Arg Gly Tyr Asp Tyr
1               5                   10

<210> SEQ ID NO 49

```
<211> LENGTH: 11
<212> TYPE: PRT
<213> ORGANISM: Llama paca

<400> SEQUENCE: 49

Tyr Arg Thr Gly Trp Gly Gly Arg Arg Gly Tyr
1               5                   10
```

TRIPLE VECTOR FOR EXPRESSING ANTIBODY MOLECULES IN FULL THERAPEUTIC FORMAT

RELATED APPLICATIONS

This application is a 35 U.S.C. § 371 filing of International Patent Application No. PCT/EP2017/075983, filed Oct. 11, 2017, which claims priority to Great Britain Patent Application No. 1617270.2, filed Oct. 11, 2016, the entire disclosures of which are hereby incorporated herein by reference in their entirety.

BACKGROUND OF THE INVENTION

1. Field of the Invention

The invention relates generally to an expression vector for use in a phage display of an antibody molecule in its therapeutic form, and more particularly to an expression vector for producing an antibody molecule comprising an Fc domain, more particularly a human Fc domain.

2. Description of the Related Art

Phage display is based on encoding the gene of interest in-frame with one of the phage coat proteins (phenotype), and encapsulates the fusion gene within the phage particle (genotype). Recombinant antibodies have been displayed on phage particles as scFv or Fab fragments. Unlike in the case of Fabs that are displayed in a monovalent manner, the polyvalent display of scFvs results in avidity effects allowing the recovery of low affinity-binders, but these same avidity effects make it difficult to select stringently on the basis of intrinsic affinity.

More recently, bivalent Fab, F(ab)'$_2$, has been displayed on phage particles in a manner that effectively resembles the binding behavior of natural IgGs [Lee et al. 2003]. Nevertheless, for the vast majority of diagnostic and therapeutic applications, antibody fragments isolated from most existing display technologies must be converted to full-length IgG, the format of choice in the clinics. This process requires additional cloning steps and the expression of the reformatted antibody gene in mammalian cells. A conspicuous drawback of the scFv format is that reformatting to IgG can result in loss of activity [Mazor et al., 2010]. Yet another disadvantage of most existing phage display systems is that the antibody gene is expressed as a fusion protein with one of the phage coat proteins. As a result, some of the antibodies isolated through library screening can only fold in the context of a fusion protein and cannot be expressed independently.

An alternative approach is the production of soluble full-length IgGs in bacteria and screening of combinatorial IgG libraries using bacterial periplasmic display. Library cells expressing intact IgGs specifically labeled with fluorescently conjugated antigen are readily distinguished and isolated by fluorescence-activated cell sorting (FACS). [Mazor et al., 2007]

Unlike phage display, FACS has the distinct advantage of relying on real-time quantitative multiparameter analysis of individual cells, allowing single-cell resolution for selection. Although FACS is a very powerful high-throughput screening methodology, sorting a library >$10^9$ cells using FACS is time-consuming and challenging [Mazor et al. 2010]. The challenge can be reduced by prescreening a library using periplasmically expressed IgG molecules that are bound to phagemid particles expressing Fc-binding ZZ protein [Mazor et al. 2010].

More recently Tesar et al. reported on a novel phagemid vector for Fab phage display that allows expression in mammalian cells without sub-cloning. The vector uses a mammalian signal sequence that drives expression of Fab fragments fused to a phage coat protein in *E. coli* and IgG expression in mammalian cells [Tesar et al. 2013]. Although the disclosed method avoids sub-cloning for mammalian expression, the phage display screening is done on Fab fragments as distinguished from full IgGs.

There is a need for a vector that allows selection by phage display of antibody molecules in an envisioned therapeutic format. There is a further need for avoiding the selection of antibody molecules that, upon fusion to an Fc domain, may lose antigen binding activity. There is yet a further need for avoiding sub-cloning for expression in bacterial periplasm. There is yet a further need for avoiding sub-cloning for expression in mammalian cells.

Thus, there is a particular need for a triple expression vector that allows selection by phage display of antibody molecules in an envisioned therapeutic format, as well as allowing expression of the antibody molecule in the envisioned therapeutic format in both bacterial periplasm and in mammalian cells.

BRIEF SUMMARY OF THE INVENTION

The present invention addresses these problems by providing a triple expression vector for expressing an antibody molecule comprising an Fc domain in prokaryotic and in eukaryotic cells, said triple expression vector comprising:
  a. a polynucleotide encoding an Fc domain protein;
  b. a polynucleotide encoding a phage coat protein;
  c. a cloning site for cloning genes coding an antibody molecule or a part thereof wherein the antibody molecule or part thereof does not include an Fc domain;
  d. a prokaryotic secretion signal sequence and a eukaryotic expression signal sequence, or a secretion signal sequence that drives efficient secretion in both prokaryotic and eukaryotic cells;
  e. a promoter for mediating expression in eukaryotic cells; and
  f. a stop codon for preventing expression of the phage coat protein in eukaryotic cells.

The expression vector can be used for expressing VHH-Fc molecules, scFv-Fc molecules, VH-Fc, VL-Fc for example.

Another aspect of the invention comprises a method for building a phage display library using the triple expression vector. Another aspect of the invention comprises a phage display library obtained with the triple expression vector. The phage display library can be used in identifying antibody molecules comprising Fc domains having binding affinity to an antigen of interest.

The method may comprise the step of establishing a molecular identity marker of an antibody molecule having affinity to the antigen of interest. The molecular identity marker may comprise amino acid sequences of one or more CDRs of the antibody molecule.

Another aspect of the invention comprises a method of producing an antibody molecule or part thereof comprising an Fc domain, the method comprising the step of expressing the triple expression vector in a prokaryotic cell, for example in the periplasm of a prokaryotic cell.

Another aspect of the invention comprises a method of producing an antibody molecule or part thereof comprising an Fc domain, the method comprising the step of expressing the triple expression vector in a eukaryotic cell, for example a mammalian cell, more particularly a human cell.

BRIEF DESCRIPTION OF THE DRAWINGS

The features and advantages of the invention will be appreciated upon reference to the following drawings, in which:

FIG. 4 shows sequences and frequency of the CDR3 regions identified in VHH antibody molecules and in VHH-Fc antibody molecules selected from the same anti-ABDEG immune repertoires.

FIG. 13 shows sequences and frequency of the anti-human CXCR4 CDR3 regions identified in VHH antibody molecules and in VHH-Fc antibody molecules selected from the same naïve repertoire.

DETAILED DESCRIPTION OF THE INVENTION

Figure 1:
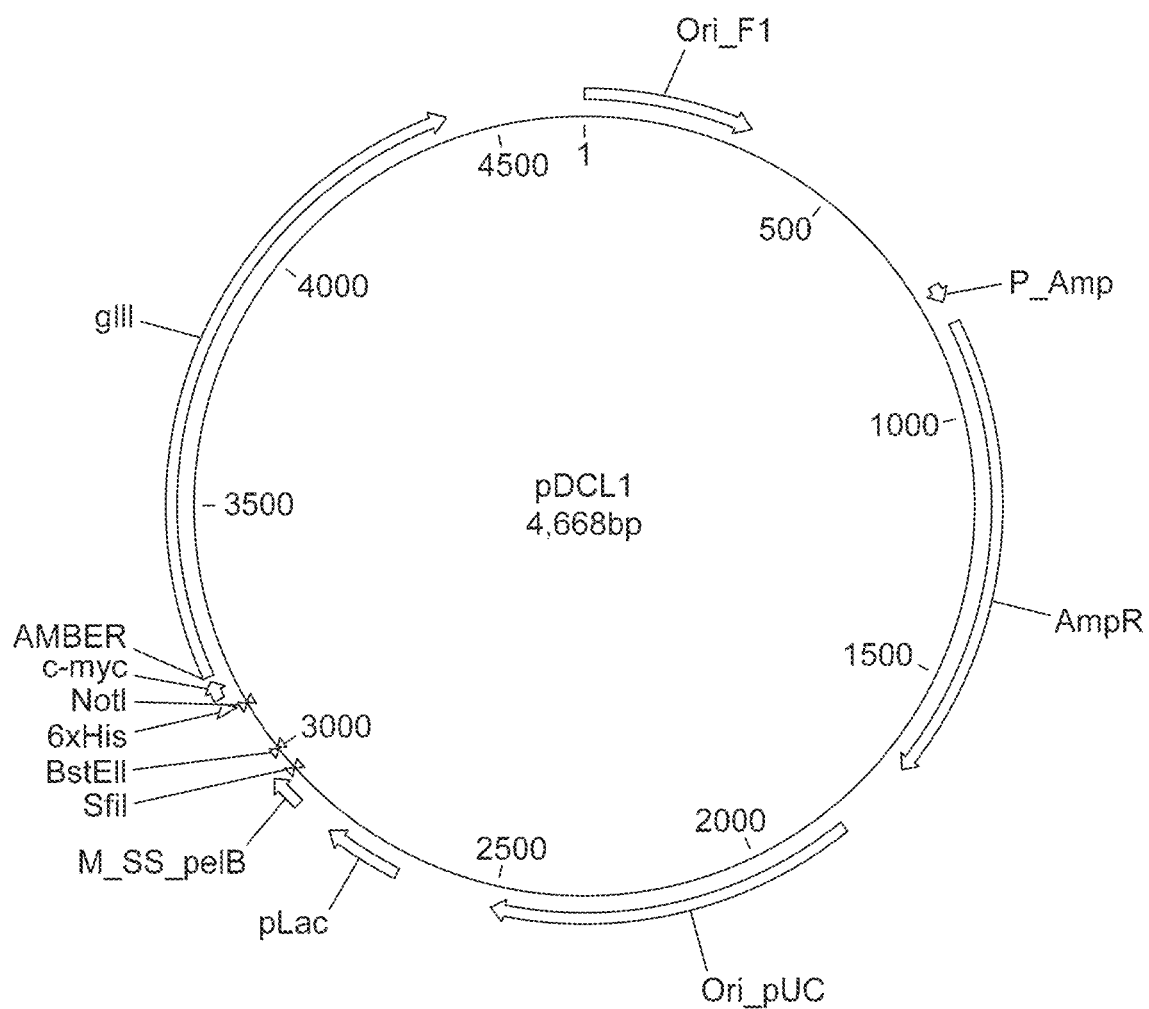
FIG. 1 is a schematic representation of expression vector pDCL1. Restriction enzyme pair BstEII/NotI is for cloning hinge Fc sequences. Restriction enzyme pair SfiI/BstEII is for cloning VHH sequences.

Phage display is a powerful tool for screening antibody molecules for binding affinity to an antigen of interest. The antibody molecules used in phage display are typically in Fab or in scFv format. When used for screening single domain antibodies (also referred to as VHH antibodies, VH antibodies, VL antibodies) the display format is typically the full single domain antibody.

The antibody molecule of therapeutic interest, however, in many cases comprises an Fc domain so that the molecule has Fc-mediated effector functions such as complement activation and/or Fc-receptor mediated phagocytic clearance. The Fc domain can be important also for the in vivo half-life of the antibody molecule. This is the case for conventional antibodies, which naturally comprise an Fc domain. Single domain antibodies, which naturally lack an Fc domain, can be provided with one by genetic fusion of the for example VHH to the Fc domain of a conventional antibody [Hmila et al., 2008].

A serious disadvantage of current phage display practice is that the screening is carried out on an antibody molecule (scFv, Fab or F(ab)'$_2$) that is different from the desired therapeutic format comprising an Fc domain. As a result, the screening of a phage display library suffers from both over-inclusion and under-inclusion of candidate molecules. Over-inclusion happens when promising antibodies are identified in a phage display screening that, upon fusion with an Fc domain, lose affinity to the target antigen. Under-inclusion happens when suitable candidate molecules are missed in the phage display screening, for example because the folding configuration does not correspond to that of the corresponding molecule comprising an Fc domain.

It is common practice to re-clone candidate molecules into a second vector for production of research quantities in prokaryotic cells, for example in the periplasm of bacteria, in particular *E. coli*. This re-cloning is time consuming, in particular if the number of candidate molecules is large.

Once one or more lead candidates have been identified, the candidate molecules are re-cloned again in mammalian cells, such as CHO cells or HEK cells. At this stage the candidate molecules are extended to their full therapeutic format, typically by gene fusion with an Fc domain, in many cases a human Fc (huFc) domain. It will be appreciated that this stage requires yet another time consuming re-cloning step.

The present invention addresses these and other issues encountered in current antibody discovery practice by providing a triple expression vector for expressing an antibody molecule comprising an Fc domain in prokaryotic and in eukaryotic cells, said triple expression vector comprising:

a. a polynucleotide encoding an Fc domain protein;
b. a polynucleotide encoding a phage coat protein;
c. a cloning site for cloning genes coding an antibody molecule or a part thereof wherein the antibody molecule or part thereof does not comprise an Fc domain;
d. a prokaryotic secretion signal sequence and a eukaryotic expression signal sequence, or a secretion signal sequence that drives efficient secretion in both prokaryotic and eukaryotic cells;
e. a promoter for mediating expression in eukaryotic cells; and
f. a stop codon for preventing expression of the phage coat protein in eukaryotic cells.

As noted above, the current screening of antibodies using phage display formats typically screens antibody molecules that lack an Fc domain. The triple vectors of the present invention are configured to allow for the cloning of antibody molecules or parts thereof that lack an Fc domain, such that these antibody molecules or parts thereof can be expressed as antibody molecules comprising an Fc domain. The genes coding for antibody molecules or parts thereof that do not comprise an Fc domain can be cloned into the triple vectors described herein in such a way that the gene can be transcribed in-frame with the polynucleotide encoding the Fc domain. This results in the expression of an antibody molecule comprising an Fc domain.

As used herein, the term "Fc domain" means the portion of a single immunoglobulin heavy chain including the CH2 and CH3 domains. The "CH2 domain" consists of the portion of the heavy chain that extends from residues 231-340 according to conventional EU antibody numbering (EU numbering system, Kabat E A et al. Sequences of Proteins of Immunological Interest. Bethesda, US Department of Health and Human Services, NIH. 1991). The amino acid sequence of the CH2 domain of human IgG1 is shown in SEQ ID NO: 2 and the encoding nucleotide sequence is shown in SEQ ID NO: 3. The "CH3 domain" consists of the portion of the heavy chain that lies C-terminal of the CH2 domain, from residues 341-446 according to conventional EU antibody numbering. The amino acid sequence of the CH3 domain of human IgG1 is shown in SEQ ID NO: 4 and the encoding nucleotide sequence is shown in SEQ ID NO: 5.

In certain embodiments, the Fc domain encoded by the vector is the Fc domain of an IgG1 antibody. In preferred embodiments, the Fc domain encoded by the vector is the Fc domain of a human IgG antibody, more preferably a human IgG1 antibody.

The term "triple expression vector" connotes the fact that the vector can be used for expressing the protein in three distinct media: in a prokaryotic cell resulting in the display of the molecule on filamentous phage surface; in the periplasm of a prokaryotic cell; and in a eukaryotic cell.

When expressed in the prokaryotic cell, the protein is fused with the simultaneously expressed phage coat protein. This expression is generally carried out in the presence of helper phage, so that phage particles are created that display the protein of interest at their surface. It should be noted that the protein comprises an Fc domain, which is expressed simultaneously with the protein. As a result, the protein displayed at the surface of the phage particles is in its full therapeutic form, and its conformation closely matches that of the desired therapeutic molecule. When used in screening, the screening results minimize over-inclusion and under-inclusion events of the type described above.

When expressed in the periplasm of a non-suppressor strain of a prokaryotic cell, for example an *E. coli* cell, the protein is expressed without the phage coat protein, due to the presence of an amber stop codon in the expression vector, for example the UAG amber stop codon. The expressed protein comprises the Fc domain protein, which is expressed simultaneously with the protein of interest.

When expressed in a eukaryotic cell, the protein is expressed without the phage coat protein, due to the presence of an appropriate amber stop codon (for example an UAG stop codon) in the expression vector. The expressed protein comprises the Fc domain protein, which is expressed simultaneously with the protein of interest.

The prokaryotic secretion signal sequence may be any sequence suitable for mediating secretion of the antibody molecules from prokaryotic cells. Prokaryotic secretion signal sequences are known in the art and any suitable prokaryotic secretion signal sequence may be used in accordance with the present invention. The eukaryotic expression signal sequence is any sequence suitable for driving the expression and secretion of proteins in eukaryotic cells. Eukaryotic expression signal sequences are known in the art and any suitable eukaryotic expression signal sequence may be used in accordance with the present invention. An exemplary eukaryotic expression signal sequence for use in the triple vectors described herein is a sequence encoding the peptide MGWSCIILFLVATATGVHS (SEQ ID NO: 10).

In an embodiment the expression vector further comprises a polyadenylation tail. Polyadenylation aids in translation in eukaryotic cells, as it protects mRNA from enzymatic degradation.

In an embodiment the expression vector further comprises a Kozak sequence (sometimes referred to as Kozak consensus sequence). The Kozak sequence plays an important role in the initiation of translation in a eukaryotic cell.

In an embodiment the promoter for mediating expression in eukaryotic cells is a CMV promoter. Examples of other suitable promoters include SV40, UBC, EF1A, PGK and CAGG.

In an example the expression vector comprises a nucleotide sequence coding an antibody hinge molecule, for example a human IgG hinge molecule, in particular a human IgG1 hinge molecule, or a portion thereof. The term "antibody hinge molecule" or "hinge region" refers to the portion of an immunoglobulin heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux K. H. et al. J. Immunol. 161:4083-90, 1998). The hinge regions of the human IgG heavy chains are shown in the table below. The vectors described herein may comprise a nucleotide sequence encoding any of these human IgG hinge sequences or parts thereof. In such embodiments, the vectors will be configured such that the nucleotide sequence coding the hinge molecule or sequence is positioned between the cloning site for the antibody molecule or part thereof lacking the Fc domain and the polynucleotide encoding the Fc domain. When the vectors are used to produce an antibody comprising an Fc domain, the hinge will be positioned between the antibody molecule or part thereof lacking the Fc domain and the Fc domain protein.

TABLE 1

Human IgG hinge sequences

| IgG | Upper hinge | Middle hinge | Lower hinge |
|---|---|---|---|
| IgG1 | EPKSCDKTHT (SEQ ID NO: 11) | CPPCP (SEQ ID NO: 12) | APELLGGP (SEQ ID NO: 13) |
| IgG3 | ELKTPLGDTTHT (SEQ ID NO: 14) | CPRCP (EPKSCDTPPPCPRCP)$_3$ (SEQ ID NO: 15) | APELLGGP (SEQ ID NO: 16) |
| IgG4 | ESKYGPP (SEQ ID NO: 17) | CPSCP (SEQ ID NO: 18) | APEFLGGP (SEQ ID NO: 19) |
| IgG2 | ERK (SEQ ID NO: 20) | CCVECPPPCP (SEQ ID NO: 21) | APPVAGP (SEQ ID NO: 22) |

Particularly preferred for use in combination with a VHH antibody molecule is a partial hinge corresponding to a human IgG1 hinge lacking the first 5 amino acid residues (SEQ ID NO: 1). The use of this partial hinge provides conformational flexibility to the molecule. It avoids the cysteine residue that is present in the first five amino acid residues of the human IgG1 hinge. In conventional antibodies this cysteine residue links the IgG light chain to the hinge. When used with a VHH molecule, which lacks a light chain, this cysteine would remain unpaired and is likely to cause unwanted dimerization.

In an embodiment the vector comprises a nucleotide sequence coding an antibody CH2 domain, for example an IgG1 CH2 domain, in particular a human IgG1 CH2 domain.

In an embodiment the vector comprises a nucleotide sequence coding an antibody CH3 domain, for example an IgG1 CH3 domain, in particular a human IgG1 CH3 domain.

Another aspect of the present invention is the triple expression vector having cloned therein a nucleotide sequence coding an antibody molecule or part thereof wherein the antibody molecule or part thereof does not comprise an Fc domain. As explained above, the Fc domain is the portion of an immunoglobulin heavy chain including the CH2 and CH3 domains. It follows that the cloning site of the vectors described herein is suitable for cloning nucleotide sequences encoding any form of antibody molecule or part thereof lacking an Fc domain, for example antibody molecules comprising or consisting of VH-CH1 domains, antibody molecules comprising or consisting of VL-CL domains. Antibody molecules and parts thereof that may be cloned into the vectors of the present invention include in particular antibody molecules selected from antibody light chain variable domains (VL domains), antibody heavy chain variable domains (VH domains), single chain Fv molecules (scFv) and Fab molecules. In preferred embodiments, the vectors described herein are used for the cloning of VHH domains i.e. the variable domains of camelid heavy chain-only antibodies. VHH domains are so-called to distinguish them from the "VH" domains of conventional heterotetrameric antibodies.

Another aspect of the invention is a method of building a phage display library of antibody molecules comprising Fc domains, the method comprising the steps of:
  cloning nucleotide sequences coding antibody molecules into the triple expression vector of the present invention, wherein the antibody molecules do not comprise Fc domains;
  combining the vector obtained in step a. with a helper phage; and
  expressing the antibody molecules comprising Fc domains in the coats of phage particles.

The antibody molecules expressed in the coats of the phage particles can be VHH-Fc molecules or scFv-Fc molecules, or VH-Fc molecules or VL-Fc molecules for example.

Another aspect of the invention is a phage display library obtained with this method. The phage display library can be an immune library or a naïve library. In a preferred embodiment the library is obtained from one or more animals of the Camelid family, for example llama paca. The phage display library can be a VHH-Fc library or an scFv-Fc or VH-Fc molecules or VL-Fc molecules library, for example.

Another aspect of the invention is a method of identifying antibody molecules having affinity to an antigen of interest. The antibody molecules comprise an Fc domain. The method comprises the steps of:
  Obtaining a phage display library as described above;
  Screening said library for antibody molecules having binding affinity to the antigen of interest.

The antibody molecules can be VHH-Fc molecules or scFv-Fc molecules or VH-Fc molecules or VL-Fc molecules, for example. The method may comprise the additional step of establishing a molecular identity marker of an antibody molecule having binding affinity for the antigen of interest. An example of a suitable identity marker comprises amino acid sequences of one or more CDRs of the antibody molecule. In a preferred embodiment the molecular identity marker comprises the amino acid sequences of all CDRs of the antibody molecule.

Another aspect of the invention is an information carrier containing the molecular identity marker of an antibody molecule. The information carrier can be any information carrier suitable for storing information pertaining to amino acid sequences.

Another aspect of the invention is a method of producing an antibody molecule or part thereof comprising an Fc domain, said method comprising the step of expressing the triple expression vector of the invention in a prokaryotic cell. For this purpose, the triple expression vector has cloned therein a nucleotide sequence coding an antibody molecule or part thereof wherein the antibody molecule or part thereof does not comprise an Fc domain. As the triple expression vector comprises a polynucleotide encoding an Fc domain protein, the antibody molecule produced by this method comprises an Fc domain.

In an embodiment, the vector is expressed in the periplasm of a prokaryotic cell.

In an embodiment the prokaryotic cell is an *E. coli* cell.

Another aspect of the invention is an antibody molecule produced in a prokaryotic cell by expression of its nucleotide sequence transfected into the triple expression vector of the invention.

Another aspect of the invention is a method of producing an antibody molecule or part thereof comprising an Fc domain, said method comprising the step of expressing the triple expression vector of the invention in a eukaryotic cell. For this purpose, the triple expression vector has cloned therein a nucleotide sequence coding an antibody molecule or part thereof wherein the antibody molecule or part thereof does not comprise an Fc domain. As the triple expression vector comprises a polynucleotide encoding an Fc domain protein, the antibody molecule produced by this method comprises an Fc domain.

In an embodiment, the eukaryotic cell is a mammalian cell.

In an embodiment the eukaryotic cell is a human cell.

Another aspect of the invention is an antibody molecule produced in a eukaryotic cell by expression of its nucleotide sequence transfected into the triple expression vector of the invention.

DESCRIPTION OF ILLUSTRATIVE EMBODIMENTS

The following is a description of certain embodiments of the invention, given by way of example only and with reference to the drawings.

Example 1 Cloning of Fc Molecules

Figure 2:
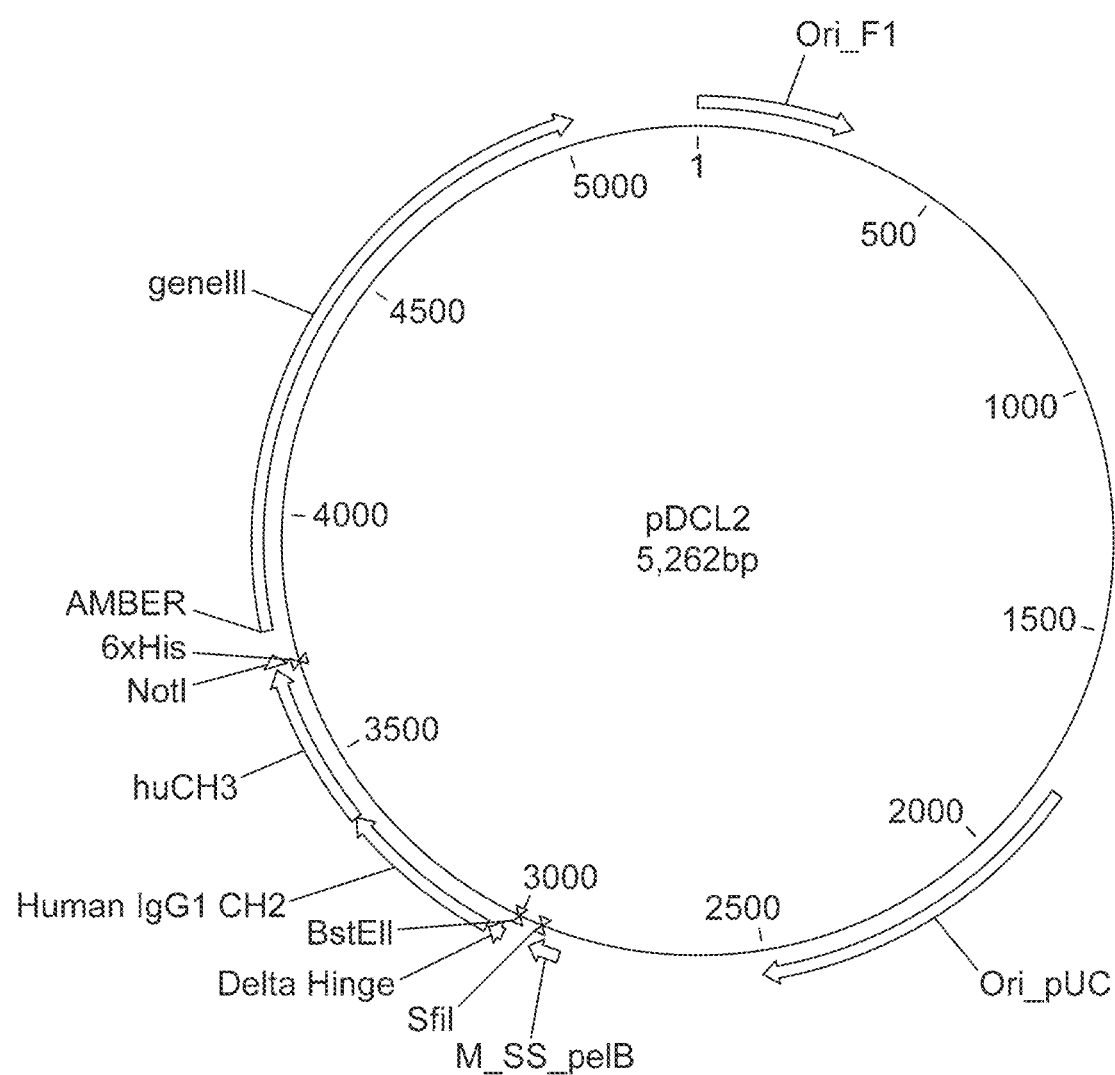
FIG. 2 is a schematic representation of expression vector pDCL2 (SEQ ID NO: 6). Restriction enzyme pair SfiI/BstEII is for cloning VHH sequences.

Starting point was our standard phage display vector that we use for phage display of Camelid heavy-chain only (VHH) antibodies. The vector, internally referred to as pDCL1 and shown in FIG. 1, was modified by introducing a cloning site for hinge-plus-Fc sequences, while retaining the cloning site for VHH sequences. The resulting vector, internally referred to as pDCL2, is shown in FIG. 2. The nucleotide sequence of pDCL2 is shown as SEQ ID NO: 6.

The following hinge-Fc sequences were used:

A modified human IgG1 hinge-Fc (pDCL2). This is the human IgG1 hinge-Fc sequence lacking the first 5 amino acid residues (see SEQ ID NO:1; SEQ ID NO: 8 is the modified hinge region encoded by the polynucleotide of SEQ ID NO:9). This is to avoid the cysteine residue that serves in the IgG1 molecule to link the light chain. This cysteine would serve no purpose in a VHH-Fc molecule, and might cause unwanted dimerization.

The pDCL2 vector was generated by inserting a synthetic polynucleotide coding for the modified huIgG1 hinge-plus-Fc into pDCL1 via BstEII/NotI. Around three micrograms of pUC57 vector containing the synthetic polynucleotide were digested with BstEII and NotI enzymes (ThermoFisher Scientific) for four hours at 37° C. The fragment of about 700 bp in length was gel purified using Macherey-Nagel Nucleospin Gel and PCR clean-up kit. 25 nanograms of the purified DNA were ligated in a 30 microliter reaction mixture with 5 Units of T4 DNA Ligase at room temperature for two hours to 50 nanograms of pDCL1 digested with BstEII and NotI enzymes and gel purified. Ligation mixture was purified using Qiagen PCR purification kit.

The purified ligation mixture was used to transform *E. coli* TOP10 using a standard heat shock protocol. One colony was isolated and sequenced. The sequence results confirmed that the modified human IgG1 hinge plus Fc was successfully cloned into the pDCL1 vector and expressed in *E. coli*.

ABDEG™ is a human IgG1 Fc molecule having three mutations in the CH2 region plus two other mutations in the CH3 region. Anti-ABDEG VHH antibodies were generated via phage display by immunizing llamas with the ABDEG molecule. Two anti-ABDEG VHH antibodies, internally referred to as 02H08 and 04H09, were selected for further experiments. The 02H08 and 04H09 VHH genes, previously selected in pDCL1 phagemid, were recovered for further cloning into pDCL2 vector via SfiI/BstEII digestion as follows: five micrograms of pDCL1 phagemid containing the VHH gene were first digested with SfiI enzyme (ThermoFisher Scientific) at 50° C. overnight. The DNA was purified from the digestion mix using Macherey-Nagel Nucleospin Gel and PCR clean-up kit and then further digested with BstEII enzyme for four hours at 37° C. The 400 bp corresponding to the VHH gene was gel-purified using the same kit as above for further ligation into pDCL2 vector.

Example 2 Phage Display and Periplasmic Expression of VHH-Fc Molecules

Starting point was the pDCL2 vector produced in Example 1. The respective genes of VHHs 02H08 and 04H09 were cloned into pDCL2 via SfiI/BstEII. A VHH antibody labeled 18F02, known not to have any affinity to ABDEG, was cloned into pDCL2 as well, to serve as a non-binding reference.

Figure 3A:
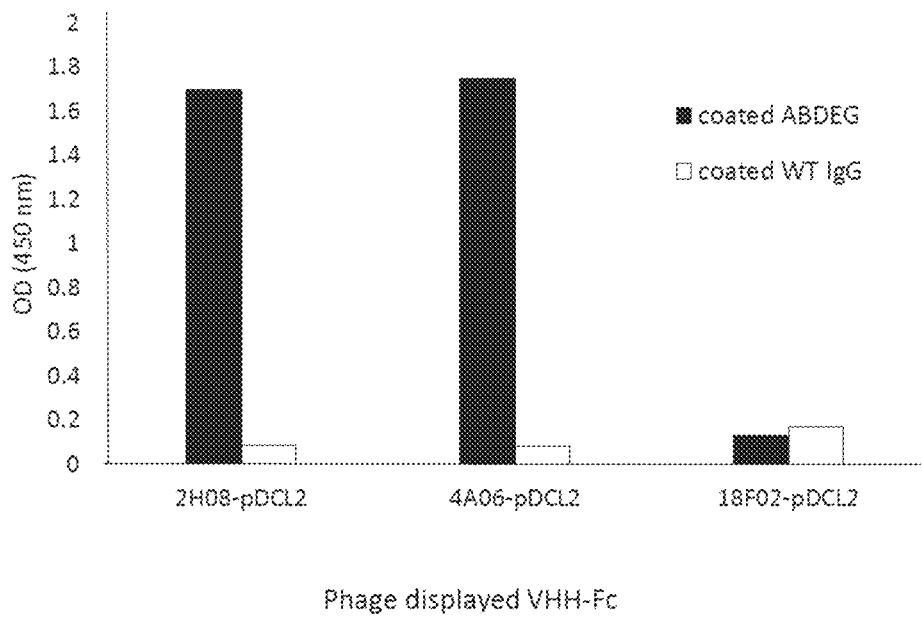
FIG. 3 shows ELISA binding results for phage displayed VHH molecules (FIG. 3A) and for soluble VHH molecules (FIG. 3B). VHH-Fc molecules bind to their antigen, the mutated Fc molecule (ABDEG) and not to wild-type Fc in IgG (WT IgG) in both formats.
Figure 3B:
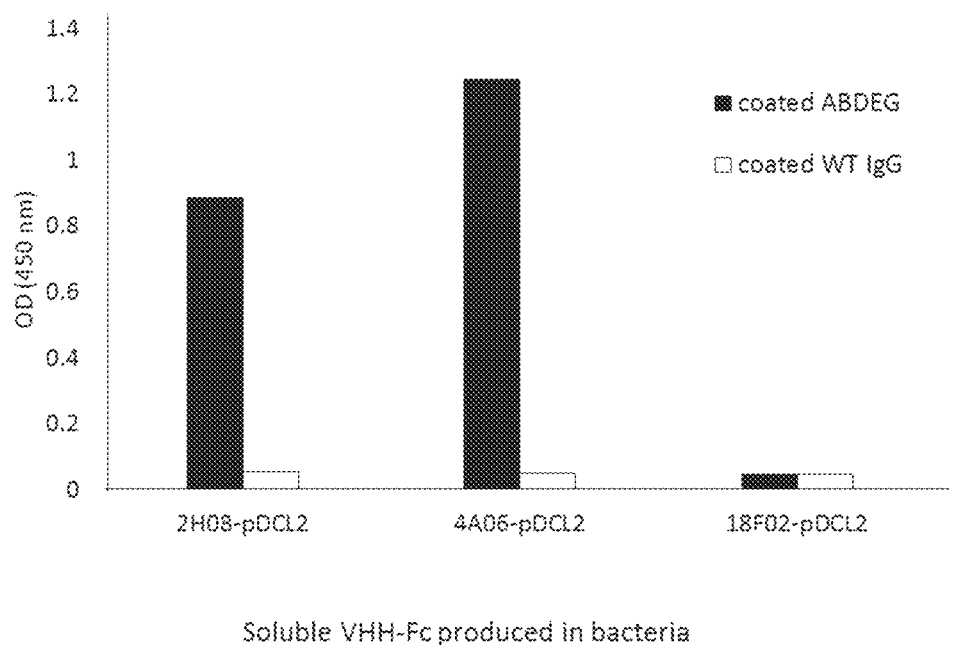

The cloned vectors were transformed in *E. coli* TG1 to produce VHH-Fc molecules displayed on phage particles, and in periplasm of *E. coli* to produce soluble c-myc tagged VHH-Fc molecules using standard protocols. Binding to the antigen was tested using ELISA (OD 450 nm). Binding of phage display antibody molecules to immobilized ABDEG in ELISA was detected using an anti-M13 HRP conjugated antibody. The results are presented in FIG. 3A. Binding of soluble antibody molecules to immobilized ABDEG in ELISA was detected using an anti-c-myc HRP conjugated antibody. Results are shown in FIG. 3B. The results show that anti-ABDEG VHHs-Fc (02H08 and 04A06) bind to antigen when displayed on phage and as soluble protein.

Example 3 Phage Display Library of VHH-Human Fc Molecules

We had previously constructed an immune library, internally referred to as SD06, of anti-ABDEG VHH antibodies. This VHH library cloned into pDCL1 was obtained by initial amplification of the VHH-CH2 regions from cDNA of an immunized llama followed by a nested PCR using SfiI-tagged framework 1 (FR1) and NotI-tagged hinge specific primers. We used this SD06 library as the starting point for the following experiments.

The gel purified VHH-CH2 amplicon obtained for the generation of SD06 library was used as template in individual nested PCR reaction using different SfiI-tagged FR1 primers and a FR4-BstEII primer The generated VHH amplicons were pooled, gel purified, digested with SfiI/BstEII, and ligated into the pDCL2 vector using similar conditions as described in Example 1 for the cloning of 02H08 and 04H09 into pDCL1. The purified ligation mixture was used for electroporation of the TG1 *E. coli* strain to generate the VHH-huFc library, internally referred to as SDhFc01, with 1.04E+08 individual clones; 100% of which have a VHH insert.

Panning of library SDhFc01 on biotinylated Fc molecules containing the ABDEG mutations in two consecutive rounds of in-solution selections, followed by binding ELISA on the same antigen using monoclonal soluble antibody molecules (binding detected via anti-c-myc HRP conjugated antibody) resulted in a selection of 136 VHH-Fc antibody molecules. From the same selection and screening scheme using the original library, SD06, 93 VHH antibodies were selected.

The CDR3 regions of the selected antibody molecules were sequenced. The sequence and frequency of the obtained CDR3 are shown in FIG. 4. From 188 selected VHH-Fc molecules, 136 specifically recognizing ABDEG, and corresponding to 12 different CDR3 sequences, were identified. By contrast, when selected in VHH format, 93 antibody molecules corresponding to 6 different CDR3 sequences were identified. Three of the different CDR3 sequences shown in antibody molecules selected as VHH-Fc were also present in antibody molecules selected as VHH. In some cases, CDR3 sequences (i.e. DLRTYYGSRDY—SEQ ID NO: 25) were identified with a higher frequency as VHH-Fc than as VHH. There are also cases where CDR3 sequences were found abundantly only in VHH-Fc molecules (i.e. IGGQFATREY—SEQ ID NO: 28). On the other hand, some CDR3 sequences very abundantly selected as VHH (i.e. LGRKPDY—SEQ ID NO: 36) were not selected as VHH-Fc.

The results show that it is possible to select VHH antibodies in VHH-Fc format. The results further show that, in cases where VHH-Fc is the desired therapeutic format, selection in this format is preferred. Selection in VHH format leads to both over-inclusion (because of selected molecules that lose binding affinity when fused to a human Fc molecule) and under-inclusion (a number of VHH-Fc molecules having good binding affinity were not identified in the VHH format).

Example 4 Expanding the Vector for Expression in Mammalian Cells

In order to make vector pDCL2 suitable for expression in mammalian cells, components of a commercially available mammalian expression vector were introduced into pDCL2.

Figure 5:
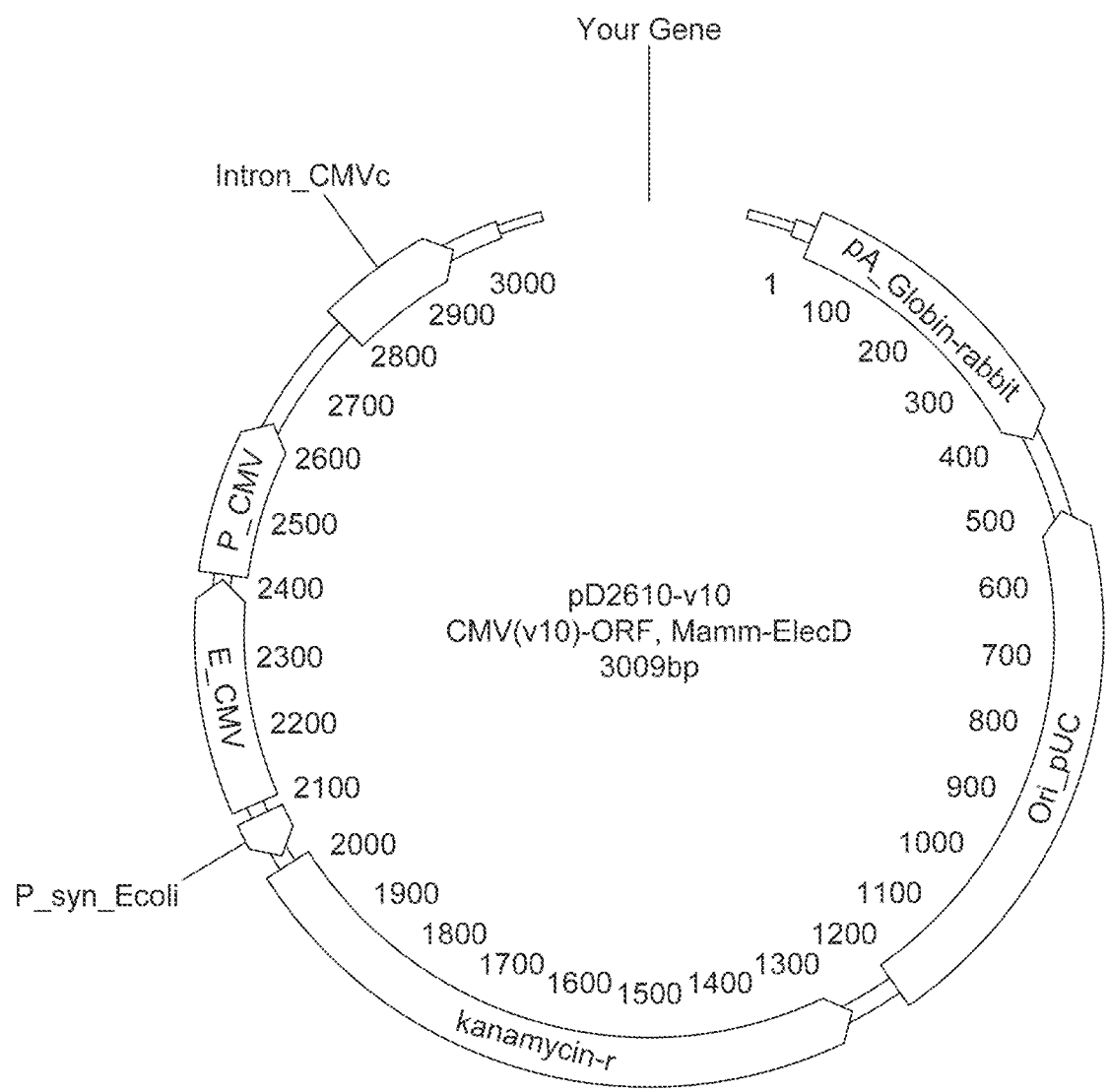
FIG. 5 is a schematic representation of mammalian expression vector pD2610-v10 from DNA 2.0

FIG. 5 shows a schematic representation of a representative mammalian expression vector. The specific vector is pD2610-v10, available from DNA 2.0 of Newark, Calif., USA.

Figure 6:
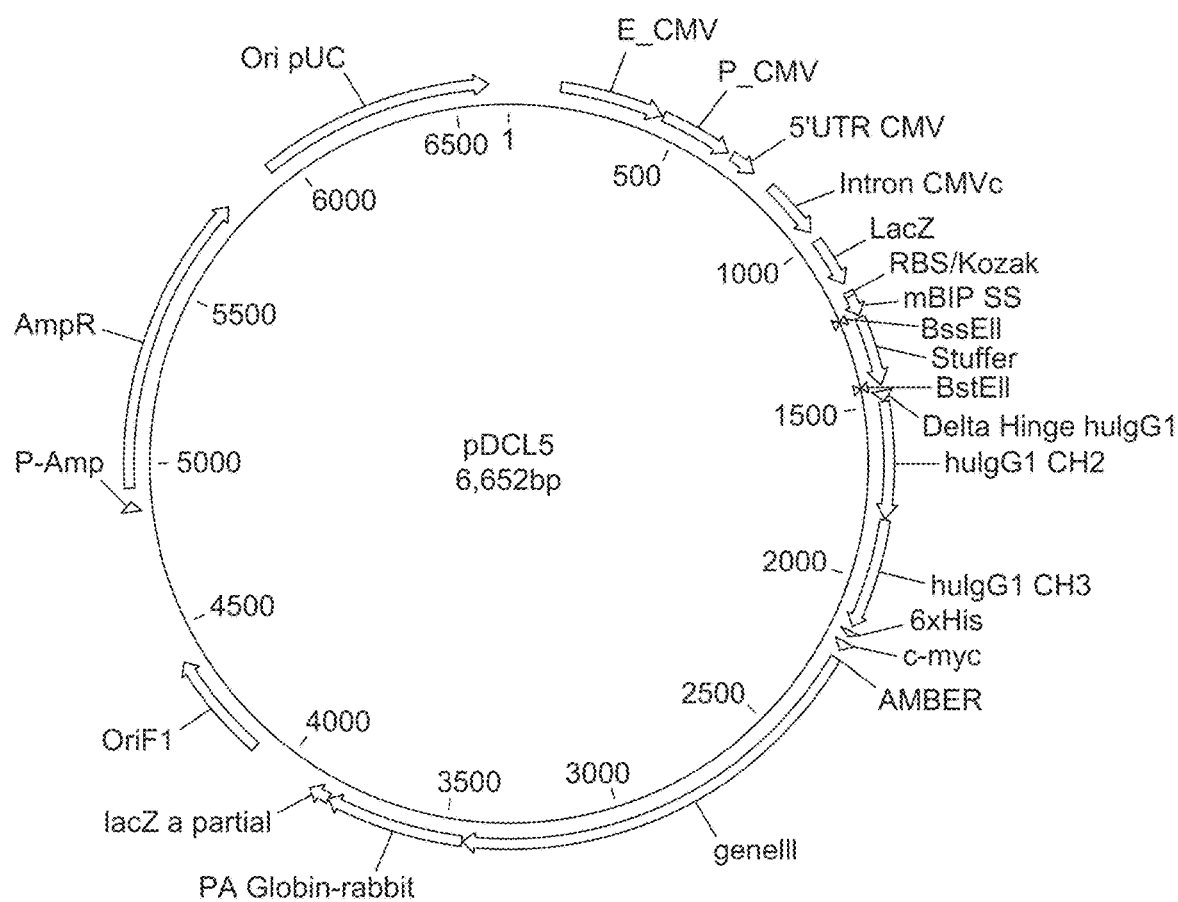
FIG. 6 is a schematic representation of expression vector pDCL5 (SEQ ID NO: 7).

FIG. 6 shows a schematic representation of the triple expression vector used in our experiments. The internal reference for this vector is pDCL5. The nucleotide sequence of pDCL5 is shown as SEQ ID NO: 7.

This vector retains all elements of the pDCL2 vector, making it suitable for expression of VHH-Fc molecules displayed on filamentous phage as well as in bacterial periplasm. Origin sequence Ori-pUC is a bacterial origin sequence. Ori-f1 is a replication origin for filamentous phage. CMV is a viral based origin sequence that is often used to drive the expression of proteins in mammalian cells. CMV was adopted from the pD2610-v10 vector, as was pA_globin rabbit (see FIG. 5). The vector comprises an amber stop codon to prevent expression of phage coat gene III when it is not desired, i.e., when the antibody molecule is expressed in periplasm of a non-suppressor bacteria strain cell or in a mammalian cell.

The vector pDCL5 is designed so that VHH genes are cloned in frame with mBiP and with human IgG1 Fc, via restriction enzyme pair BstEII and BssHII. Signal peptide mBiP is as described in *Protein Engineering & Design.* 2013, 26:655-662. The vector encodes ampicillin resistance as a selection marker.

Example 5 Expression of VHH-Fc Molecules in the pDCL5 Vector

A llama VHH naïve library had been previously constructed by amplifying first VHH-CH2 genes from ten non-immunized llamas and by finally cloning the VHH genes into pDCL1 vector. Four different anti-CXCR4 VHH molecules, 7A11, 7G04, 7F04, 7E10, 7B05; and one anti-HER2 VHH molecule, 3C04 isolated from the VHH naïve library were selected for further experiments The VHH sequences were PCR amplified using a BssHII tagged forward primer and a BstEII reverse primer. The amplicons were digested with BssHII and BstEII (ThermoFisher Scientific) at 37° C. for 4 hours, and ligated into the pDCL5 previously digested with the same restriction enzymes. The cloned vectors were used to transform TG1 cells. The VHH-huFc sequences were confirmed by plasmid DNA sequencing using a primer annealing in the lacZ sequence of pDCL5 and with a primer annealing in the CH2 sequence of pDCL5.

Phage displaying VHH-Fc molecules and periplasmic extract containing soluble VHH-Fc molecules, prepared from 10 ml *E. coli* cultures according standard protocols, were tested for binding to Virus Like Particles displaying CXCR4 (CXCR4 VLPs) and to control VLPs non displaying CXCR4 (Null VLPs) in ELISA. Anti-HER 2 VHH-Fc molecule (3C04) was tested for binding HER2 protein. In addition, soluble VHH-Fc molecules were also tested for binding to HEK293T WT cells and to HEK293T cells transfected with CXCR4 or with HER2.

Figure 7A:
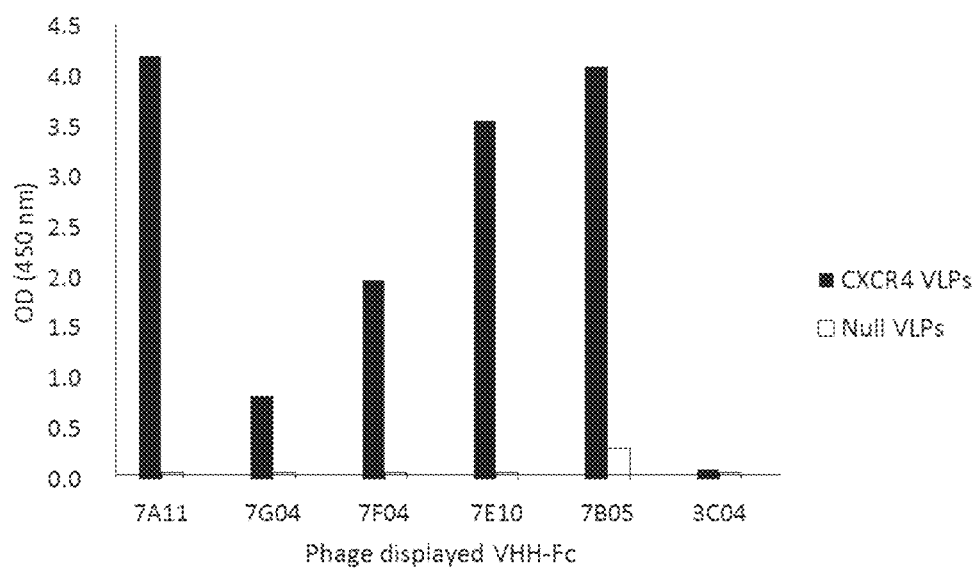
FIG. 7A shows ELISA results for binding to human CXCR4 VLPs and to Null VLPs of phage displayed anti-human CXCR4 VHH-Fc molecules and of an anti-HER2 VHH-Fc molecule (3C04) expressed from vector pDCL5.
Figure 7B:
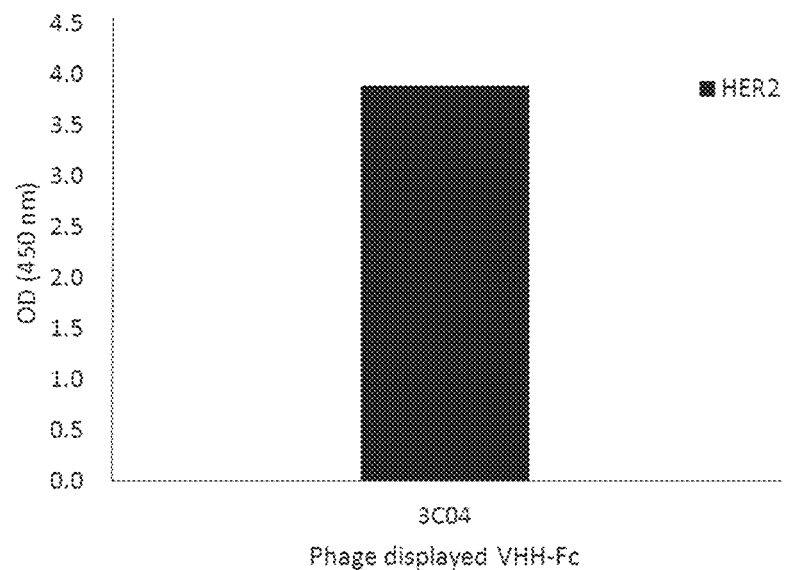
FIG. 7B shows ELISA results for binding to HER2 of a phage displayed anti-HER2 VHH-Fc molecule (3C04) expressed in bacteria from vector pDCL5.
Figure 8A:
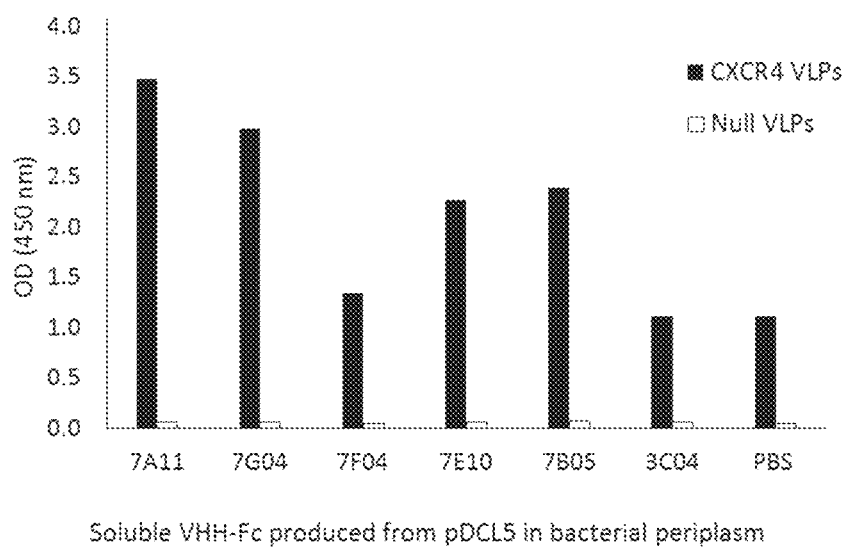
FIG. 8A shows ELISA results for binding to human CXCR4 VLPs and to Null VLPs of soluble anti-human CXCR4 VHH-Fc molecules and of an anti-HER2 VHH-Fc molecule (3C04) expressed in bacteria from vector pDCL5.
Figure 8B:
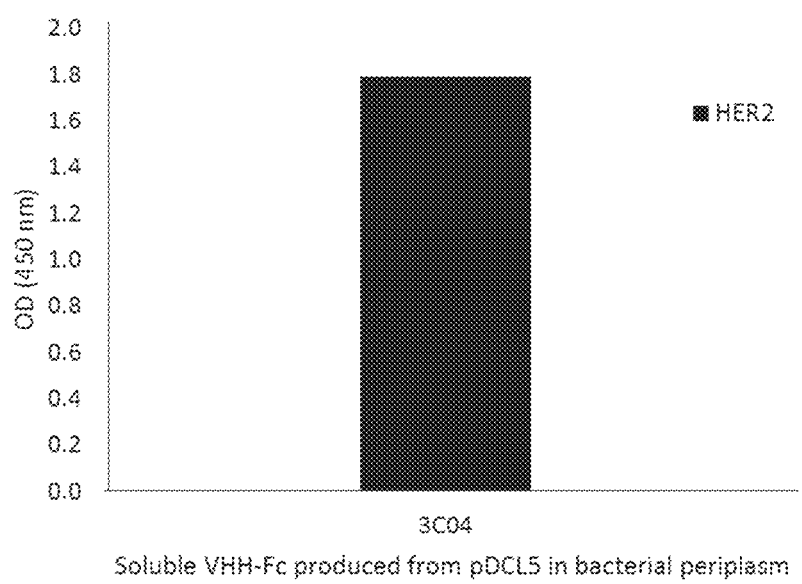
FIG. 8B shows ELISA results for binding to HER2 of a soluble anti-HER2 VHH-Fc molecule expressed in bacteria from vector pDCL5.
Figure 9:
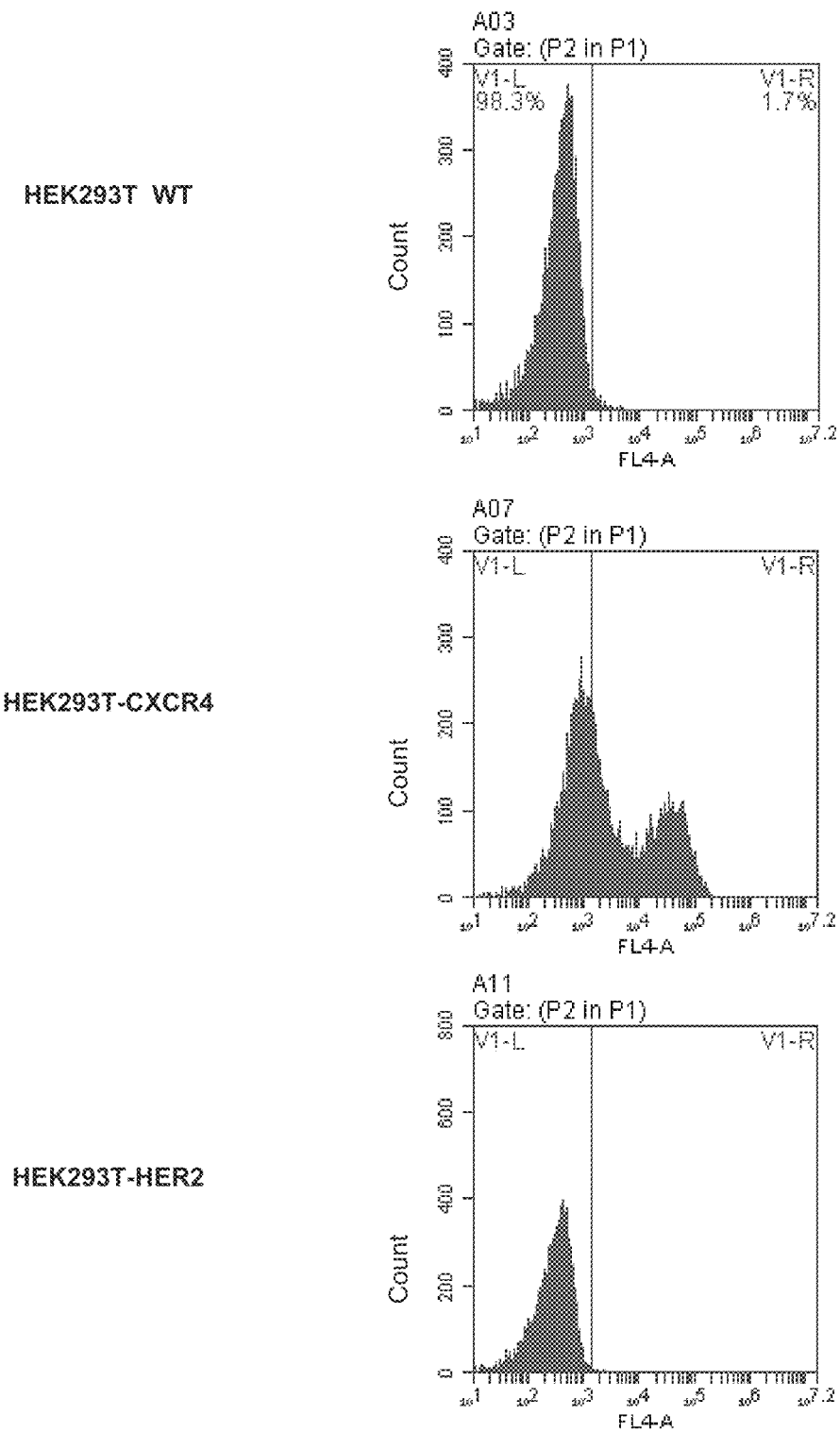
FIG. 9 shows FACS results (histograms) for binding of soluble anti-human CXCR4 VHH-Fc molecules and of an anti-HER2 VHH-Fc molecule expressed in bacteria from vector pDCL5 to HEK293T WT and to HEK293T cells transfected with human CXCR4 or with HER2.
Figure 9:
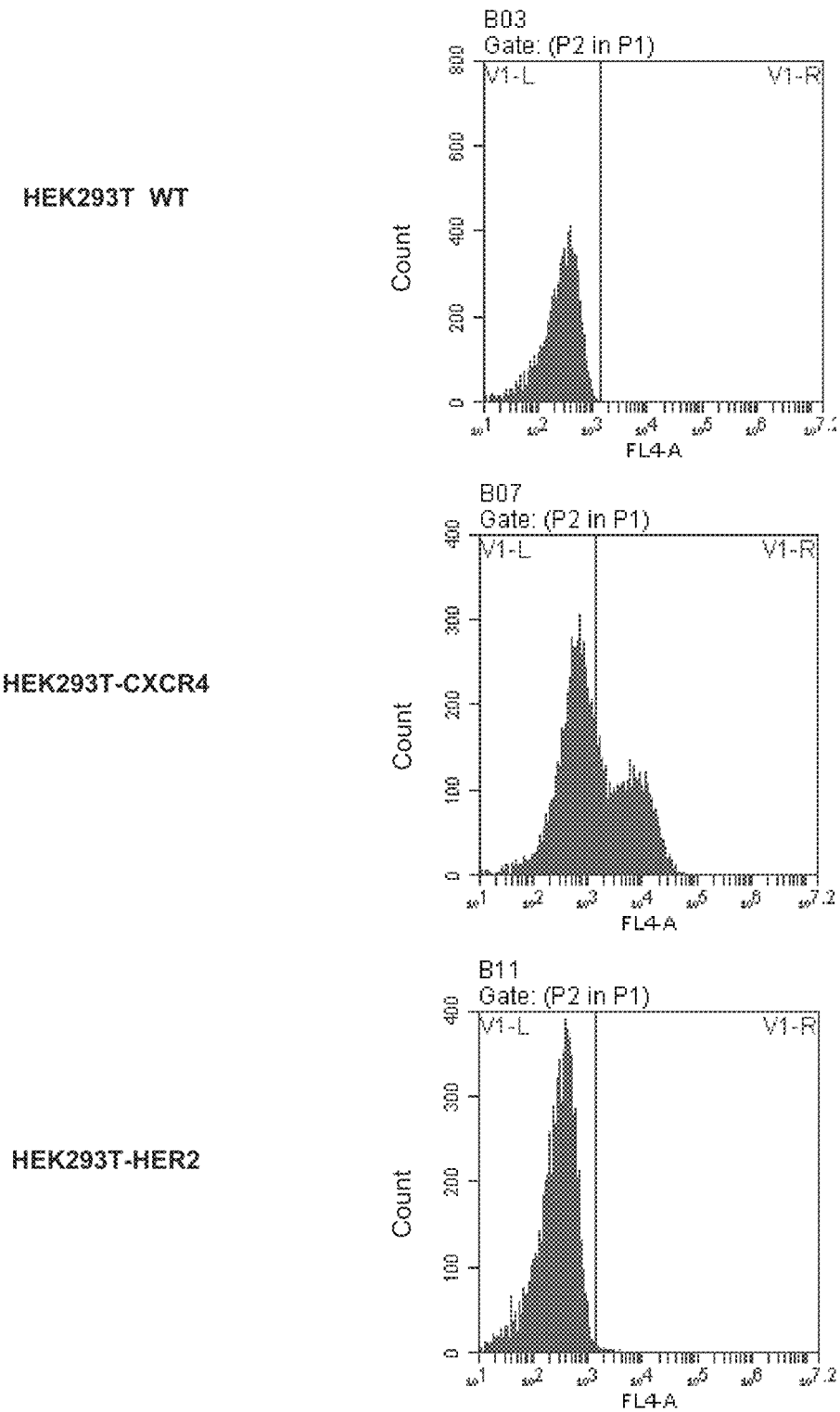
Figure 9:
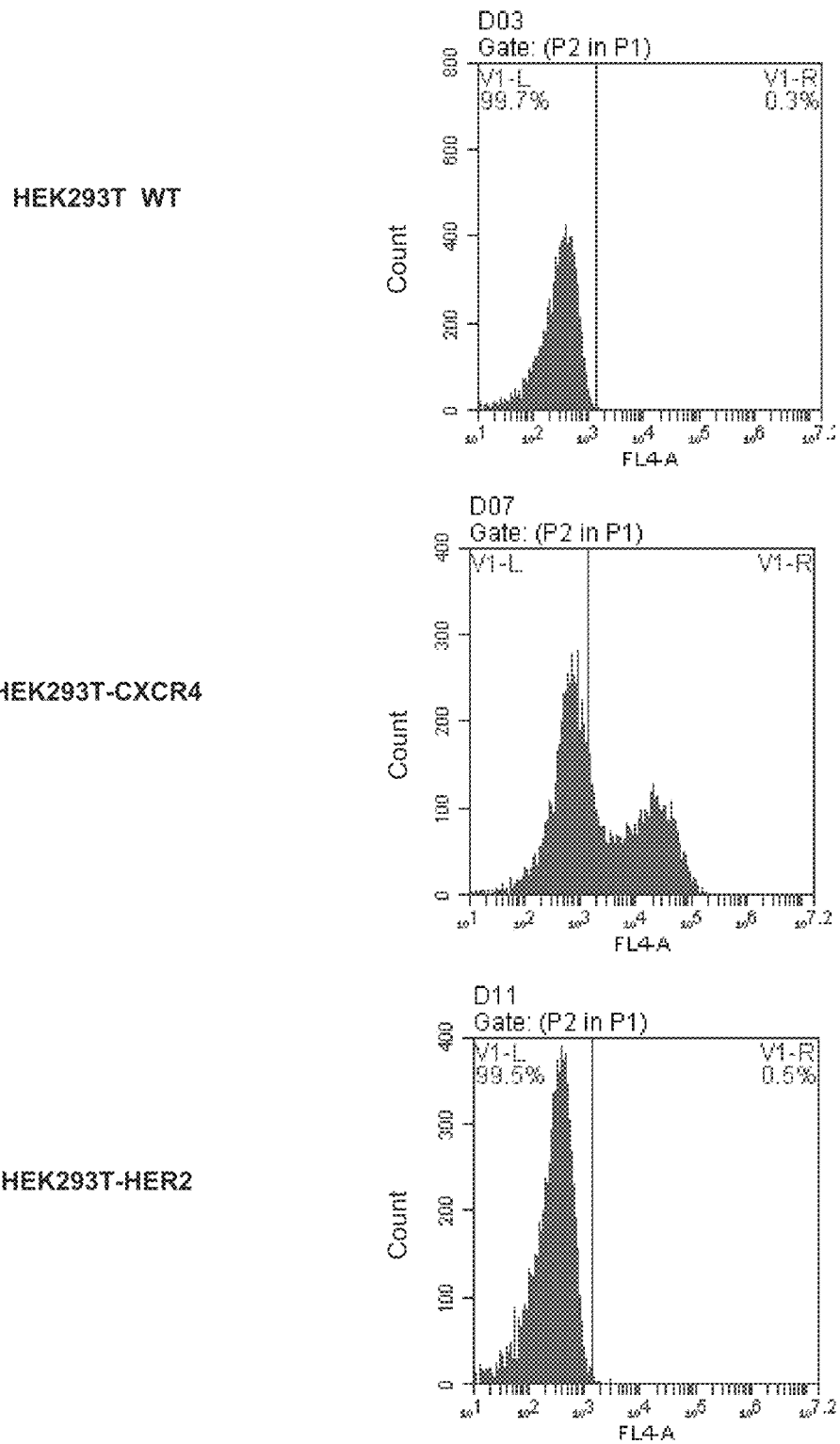

In ELISA binding of phage display antibody molecules was detected using an anti-M13 HRP conjugated antibody (FIGS. 7A and 7B) while bound soluble antibody molecules were detected using a mouse anti-c-myc antibody followed by an anti-mouse IgG HRP conjugated antibody (FIGS. 8A and 8B). In FACS, binding of soluble antibody molecules was detected using a mouse anti-c-myc antibody and a goat anti-mouse APC conjugated antibody (FIG. 9).

Figure 10:
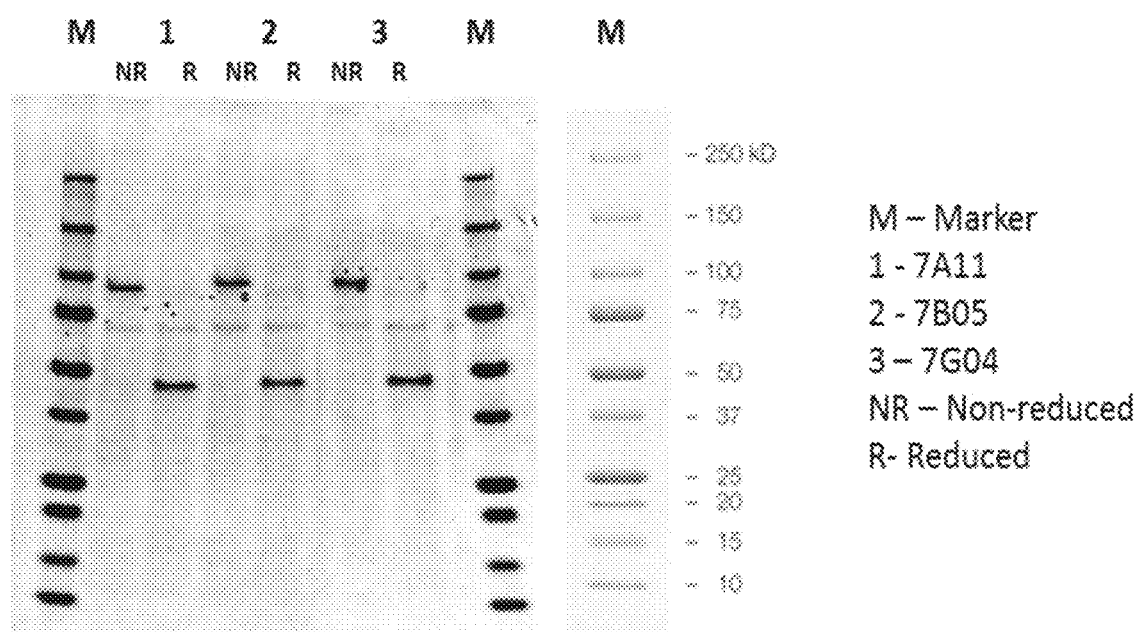
FIG. 10 shows the results of SDS-PAGE analysis of conditioned medium from cultures of HEK293FF cells transiently transfected with triple vector pDCL5 containing anti-human CXCR4 VHH-Fc molecules 7A11, 7B05 and 7G04.
Figure 11:
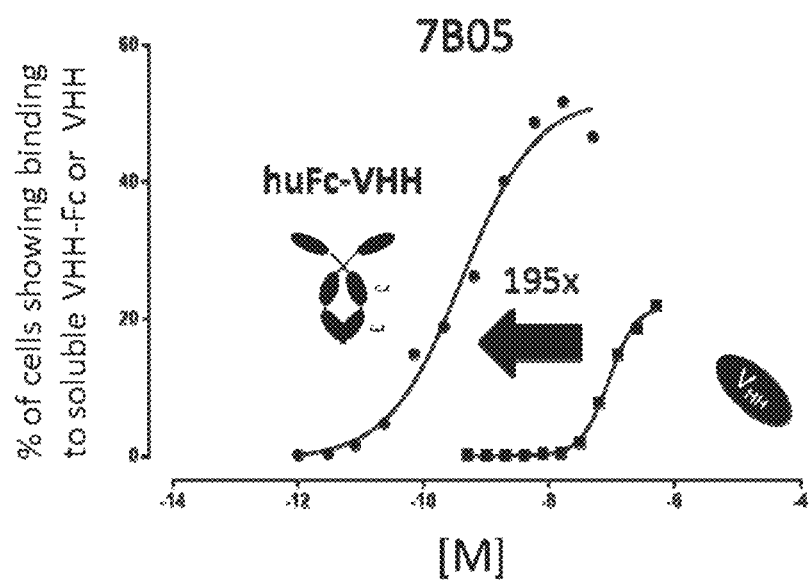
FIG. 11 shows FACS results for titration of binding to HEK293T cells transfected with human CXCR4 of purified anti-human CXCR4 VHH-Fc molecules 7A11, 7B05 and 7G04 produced in HEKFF cells from pDCL5 as well as of purified anti-human CXCR4 VHH molecules 7A11, 7B05 and 7G04 produced in bacteria and the calculated EC50 values.

Plasmid DNA from anti-CXCR4 VHH-Fc antibodies 7A11, 7B05 and 7G04 were used to transfect HEK293FF cells using PEI as transfection reagent. Four days after transfection cell culture supernatant were collected and the presence of soluble VHH-Fc was analyzed by sodium dodecyl sulfate polyacrylamide gel electrophoresis (SDS-PAGE) under reducing (R) and non-reducing conditions (NR). The results are presented in FIG. 10. The bands migrating as 80 KDa molecular weight proteins under non reducing conditions and as 40 KDa protein under reducing conditions confirm the successful production of VHH-Fc. The VHH-Fc antibodies were purified using sepharose-protein A beads and concentrated in PBS as final buffer using centrifugal filter concentrators. The purified VHH-Fc molecules were titered in FACS for binding to HEK cells transfected with CXCR4 using a mouse anti-c-myc antibody and a goat anti-mouse APC conjugated antibody. EC50 values were determined using GraphPrism® software. For comparison the binding of purified anti-CXCR4 VHH 7A11, 7B05 and 7G04 produced in bacteria was also titered. Results are shown in FIG. 11 and in the table below.

TABLE 2

|  | 7A11 VHH | 7A11 VHH-Fc | 7B05 VHH | 7B05 VHH-Fc | 7G04 VHH | 7G04 VHH-Fc |
| --- | --- | --- | --- | --- | --- | --- |
| EC50 (nm) | 13 | 0.27 | 78 | 0.40 | 18 | 1.34 |

NB 45-77% of the transfected cells expressed human CXCR4 as stained with 12G5 anti-CXCR2 antibody Example 6 Construction of a VHH-Fc Naïve Library in the pDCL5 Vector We had previously constructed a VHH naïve library from which the anti-CXCR4 and anti-HER2 VHH antibodies described in example 5 were isolated. We used this VHH naïve library as the starting point for the following experiments.

Approximately 100 micrograms of pDCL5 DNA were digested first with BstEII restriction enzyme (NEB) at 60° C. for three hours. The digested and gel-purified plasmid was further digested with BssHII restriction enzyme (NEB) at 50° C. for 16 hours and gel-purified again.

The gel purified VHH-CH2 amplicons obtained for the generation of the VHH naïve library described in Example 5 were used as template in individual nested PCR reaction using different BssHII-tagged FR1 primers nd a FR4-BstEII primer.

The amplicons of the nested PCR were subjected to BssHI (NEB) digestion at 50° C. for two followed by digestion with BstEII (NEB) at 60° C. for two hours.

Figure 12A:
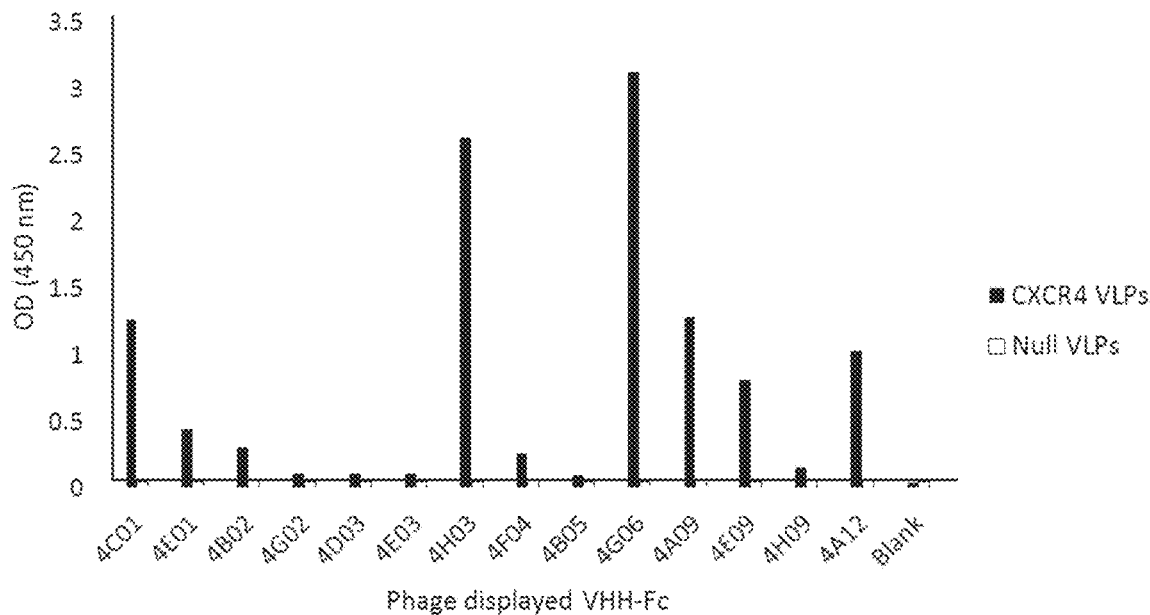
FIG. 12A shows the ELISA results for binding to human CXCR4 and Null VLPs of phage displayed VHH-Fc molecules selected from the VHH-Fc Naïve Library and expressed in bacteria from vector pDCL5.
Figure 12B:
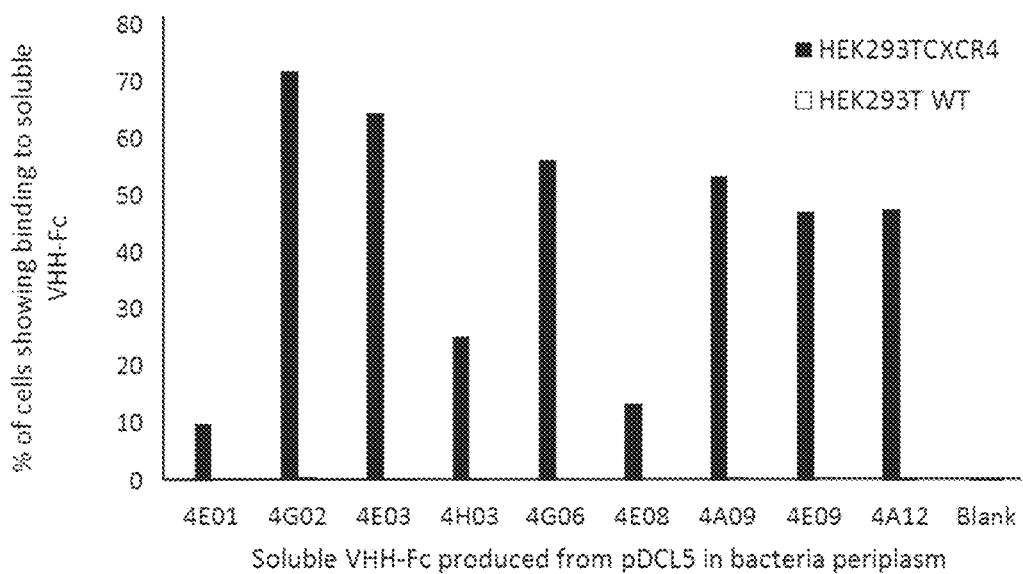
FIG. 12B shows the FACS results for binding to HEK WT and to HEK cells transfected with human CXCR4 of soluble VHH-Fc molecules selected from the VHH-Fc Naïve Library and expressed in bacteria from vector pDCL5.

The digestion mixes were purified using Macherey-Nagel Nucleospin Gel and PCR clean-up kit and ligated into the pDCL5 vector previously digested with the same restriction enzymes. The purified ligation mixtures were used for electroporation of the TG1 E. coli strain to generate the VHH-huFc library, internally referred to as VHH-Fc Naïve Library, with 1.33E+09 individual clones; 98% of which have a VHH-Fc insert Example 7 Panning of VHH-Fc Naïve Library in pDCL5 Vector and Expression of Selected VHH-Fc Molecules in Bacteria and Mammalian Cells VHH-Fc Naïve Library was panned against CXCR4 VLPs in three consecutive rounds of selections. Selected clones were tested in binding ELISA (OD 450 nm) on CXCR4 VLPs and on Null VLPs using phage displayed VHH-Fc molecules that were produced using standard protocols. The binding of phage was detected using an anti-M13 HRP conjugated antibody. The results for some human CXCR4 specific clones are presented in FIG. 12A. The selected clones were also tested as monoclonal soluble antibody molecules produced in bacterial periplasm for binding to HEK WT cells and to HEK cells transfected with human CXCR4 using a mouse anti-c-myc antibody and a goat anti-mouse APC conjugated antibody. The results for some human CXCR4 specific clones are presented in FIG. 12B.

The CDR3 regions of the selected VHH-Fc molecules were sequenced and five different CDR3 sequences were identified. When an existing VHH Naïve library generated in pDCL1 vector was previously panned and screened in a similar scheme to the ones used for VHH-Fc Naïve library, 10 different CDR3 sequences were identified. The sequence and frequency of the obtained CDR3 results are presented shown in FIG. 13. Two of the different anti-human CXCR4 CDR3 sequences shown in antibody molecules selected as VHH-Fc from pDCL5 were also present in antibody molecules selected as VHH. In some cases, CDR3 sequences (i.e. PLQRPWGSGDY—SEQ ID NO: 40) were identified with a higher frequency as VHH-Fc than as VHH. Also the opposite was observed as some CDR3 sequences found from both libraries (i.e. RVAGERLHRGRQYEFDY—SEQ ID NO: 41) showed a higher frequency as VHH On the other hand, some CDR3 sequences selected as VHH (i.e. YRTGWGGRRGY—SEQ ID NO: 49) were not selected as VHH-Fc. But also, CDR3 sequences selected as VHH-Fc (i.e. DREVSGSGSRWRGTFWDY—SEQ ID NO: 39) were not selected as VHH).

Figure 14:
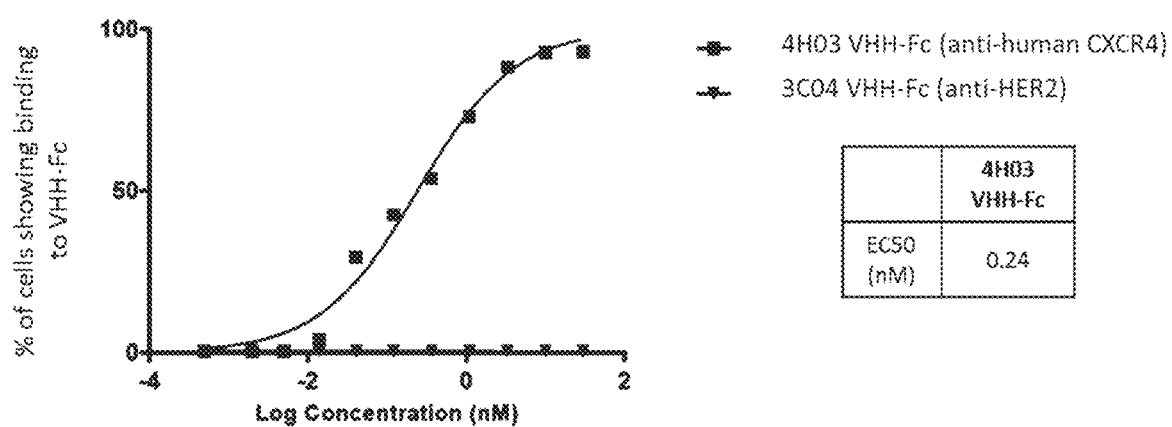
FIG. 14 shows FACS results for titration of binding to HEK cells transfected with human CXCR4 of purified anti-human CXCR4 VHH-Fc molecule 4H03, selected from VHH-Fc Naïve Library and produced in HEK cells from pDCL5, and the calculated EC50 value. The anti-HER2 VHH-Fc 3C04 was used as irrelevant molecule in this assay.

The results show that it is possible to select VHH antibodies in VHH-Fc format from a naïve repertoire. As in Example 3, these results further show that, in cases where VHH-Fc is the desired therapeutic format, selection in this format is preferred. Selection in VHH format leads to both over-inclusion (because of selected molecules that lose binding affinity when fused to a human Fc molecule) and under-inclusion (a number of VHH-Fc molecules having good binding affinity were not identified in the VHH format).

pDCL5 DNA from anti-human CXCR4 VHH-Fc antibody 4H03, corresponding to a CDR3 only selected as VHH-Fc and not as VHH (DREVSGSGSRWRGTFWDY—SEQ ID NO: 39) was used to transfect HEK293FF cells using PEI as transfection reagent. Five days after transfection cell culture supernatant were collected and the presence of soluble VHH-Fc was analyzed by sodium dodecyl sulfate polyacrylamide gel electrophoresis (SDS-PAGE) under reducing (R) and non-reducing conditions to confirm the successful production of VHH-Fc. The VHH-Fc antibody was purified using HiTrap ProteinG column in ÄKTA pure 25 system and concentrated in PBS as final buffer using centrifugal filter concentrators. The purified VHH-Fc molecule was titered in FACS for binding to HEK cells transfected with human CXCR4 using an anti-human Fc FITC antibody and EC50 value was determined using GraphPrism® software. The anti-HER2 VHH-Fc 3C04 was used as irrelevant molecule in this assay. Results are shown in FIG. 14.

Example 8 Expression of scFv-Fc in Phage Display Format

For the display of scFv-Fc in a triple vector the starting points are VH and VL amplified repertoires that are spliced together to form scFvs and a pDCL5-derived vector.

To generate the scFv spliced repertoires, the PCR amplified VH and VL (Vκ and Vλ) are combined in a PCR reaction introducing a $(G_nS_n)_n$ linker (for example $(G_4S_1)_{15}$) and restriction enzyme sequences at 5' and 3'regions for compatible cloning into the triple vector.

A triple vector for expression of scFv-Fc molecules is generated from pDCL5 by introducing restriction enzyme sequences to allow the cloning of scFv in frame with the signal peptide and the hinge plus Fc sequences.

The cloned triple vector (pDCL5 derived) containing the scFv genes is transformed into E. coli TG1 and phage particles displaying scFv-Fc molecules are produced using standard protocols.

Example 9 Expression of VH-Fc or VL-Fc in Phage Display Format

For the display of VH-Fc or VL-Fc, VH or VL repertoires are PCR amplified introducing restriction enzyme sequences at 5' and 3'regions of the V gene for compatible cloning into a triple vector.

A triple vector for expression of VH-Fc or VL molecules is generated from pDCL5 by introducing restriction enzyme sequences to allow the cloning of VH or VL in frame with the signal pepide and the hinge plus Fc sequences.

The cloned triple vector (pDCL5 derived) containing the VH or VL genes is transformed into E. coli TG1 and phage particles displaying VH-Fc or VL-Fc molecules are produced using standard protocols.

Example 10 Expression of scFv-Fc or VH-Fc or VL-Fc in Bacterial Periplasm scFv-Fc or VH-Fc or VL-Fc molecules are produced from the triple vector as soluble molecules in perisplasm of E. coli using standard protocols as in Example 2.

Example 11 Expression of scFv-Fc or VH-Fc or VL-Fc in Mammalian Cells scFv-Fc or VH-Fc or VL-Fc molecules are produced from the triple vector in mammalian cells (for example HEK293FF cells) by transfecting cells with standard reagents (for example PEI). Four to five days after transfection, scFv-Fc or VH-Fc or VL-Fc molecules are purified from the cells culture supernatant via protein A as in Example 5.

---

SEQUENCE LISTING/COMPUTER PROGRAM LISTING

Here we list the SEQENCE IDs referred to in the text

SEQ ID NO: 1-the modified huIgG1 hinge-plus-Fc
DKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK SEQ ID NO: 2-amino acid sequence of human IgG1 CH2 domain
APELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAK SEQ ID NO: 3-nucleotide sequence encoding human IgG1 CH2 domain
GCCCCGGAGCTCCTGGGCGGTCCTTCCGTGTTCCTCTTTCCGCCAAAGCCGAAAG
ATACCTTGATGATTAGCAGAACCCCGGAGGTGACGTGCGTCGTGGTCGACGTGTC
CCACGAGGATCCGGAAGTCAAGTTCAATTGGTACGTCGACGGTGTGGAGGTGCA
CAACGCCAAGACCAAGCCGAGAGAGGAGCAGTACAACTCCACCTACCGCGTCGT
GAGCGTGCTGACCGTGCTGCACCAAGACTGGTTGAACGGCAAGGAATACAAGTG
CAAGGTGTCGAACAAGGCCCTGCCGGCCCCGATCGAAAAGACCATTAGCAAGGC
GAAG SEQ ID NO: 4-amino acid sequence of human IgG1 CH3 domain
GQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK SEQ ID NO: 5-nucleotide sequence encoding human IgG1 CH3 domain
GGCCAGCCGCGCGAGCCGCAAGTGTACACCCTCCCGCCATCACGGGATGAGCTG
ACCAAGAACCAGGTGTCCTTGACGTGTCTGGTCAAGGGCTTCTACCCGAGCGACA
TTGCCGTGGAGTGGGAATCCAACGGCCAGCCGGAAAACAACTATAAGACCACCC
CACCTGTGCTTGACTCCGATGGTTCCTTCTTCCTGTACTCCAAGCTGACGGTGGAT
AAGTCCCGCTGGCAGCAGGGTAACGTGTTTAGCTGCTCAGTCATGCACGAAGCCC
TGCACAACCACTACACCCAGAAGTCACTGTCCCTGTCGCCAGGCAAA SEQ ID NO: 6-pDCL2
GCATTAAGCGCGGCGGGTGTGGTGGTTACGCGCAGCGTGACCGCTACACTTGCCA
GCGCCTTAGCGCCCGCTCCTTTCGCTTTCTTCCCTTCCTTTCTCGCCACGTTCGCCG
GCTTTCCCCGTCAAGCTCTAAATCGGGGGCTCCCTTTAGGGTTCCGATTTAGTGCT
TTACGGCACCTCGACCCCAAAAAACTTGATTTGGGTGATGGTTCACGTAGTGGGC
CATCGCCCTGATAGACGGTTTTTCGCCCTTTGACGTTGGAGTCCACGTTCTTTAAT
AGTGGACTCTTGTTCCAAACTGGAACAACACTCAACTCTATCTCGGGCTATTCTTT
TGATTTATAAGGGATTTTGCCGATTTCGGTCTATTGGTTAAAAAATGAGCTGATTT
AACAAAAATTTAACGCGAATTTTAACAAAATATTAACGTTTACAATTTTATGGTG
CAGTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACA
GACAAGCTGTGACCGTCTCCGGGAGCTGCATGTGTCAGAGGTTTTCACCGTCATC
ACCGAAACGCGCGAGACGAAAGGGCCTCGTGATACGCCTATTTTTATAGGTTAAT
GTCATGATAATAATGGTTTCTTAGACGTCAGGTGGCACTTTTCGGGGAAATGTGC
GCGGAACCCCTATTTGTTTATTTTTCTAAATACATTCAAATATGTATCCGCTCATG
AGACAATAACCCTGATAAATGCTTCAATAATATTGAAAAAGGAAGAGTATGAGT
ATTCAACATTTCCGTGTCGCCCTTATTCCCTTTTTTGCGGCATTTTGCCTTCCTGTT
TTTGCTCACCCAGAAACGCTGGTGAAAGTAAAAGATGCTGAAGATCAGTTGGGT
GCCCGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGG
CGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGG
ATGGCATGACAGTAAGAGAATTATGCAGTGCTGCCATAACCATGAGTGATAACA
CTGCGGCCAACTTACTTCTGACAACGATCGGAGGACCGAAGGAGCTAACCGCTTT
TTTGCACAACATGGGGGATCATGTAACTCGCCTTGATCGTTGGGAACCGGAGCTG
AATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGG
CCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTT
ATCTACACGACGGGGAGTCAGGCAACTATGGATGAACGAAATAGACAGATCGCT
GAGATAGGTGCCTCACTGATTAAGCATTGGTAACTGTCAGACCAAGTTTACTCAT
ATATACTTTAGATTGATTTAAAACTTCATTTTTAATTTAAAAGGATCTAGGTGAAG
ATCCTTTTTGATAATCTCATGACCAAAATCCCTTAACGTGAGTTTTCGTTCCACTG
AGCGTCAGACCCCGTAGAAAAGATCAAAGGATCTTCTTGAGATCCTTTTTTTCTG
CGCGTAATCTGCTGCTTGCAAACAAAAAAACCACCGCTACCAGCGGTGGTTTGTT
TGCCGGATCAAGAGCTACCAACTCTTTTTCCGAAGGTAACTGGCTTCAGCAGAGC
GCAGATACCAAATACTGTTCTTCTAGTGTAGCCGTAGTTAGGCCACCACTTCAAG
AACTCTGTAGCACCGCCTACATACCTCGCTCTGCTAATCCTGTTACCAGTGGCTGC

SEQUENCE LISTING/COMPUTER PROGRAM LISTING

Here we list the SEQENCE IDs referred to in the text

```
TGCCAGTGGCGATAAGTCGTGTCTTACCGGGTTGGACTCAAGACGATAGTTACCG
GATAAGGCGCAGCGGTCGGGCTGAACGGGGGGTTCGTGCATACAGCCCAGCTTG
GAGCGAACGACCTACACCGAACTGAGATACCTACAGCGTGAGCTATGAGAAAGC
GCCACGCTTCCCGAAGGGAGAAAGGCGGACAGGTATCCGGTAAGCGGCAGGGTC
GGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTC
AGGGGGGCGGAGCCTATGGAAAAACGCCAGCAACGCGGCCTTTTTACGGTTCCT
GGCCTTTTGCTGGCCTTTTGCTCACATGTTCTTTCCTGCGTTATCCCCTGATTCTGT
GGATAACCGTATTACCGCCTTTGAGTGAGCTGATACCGCTCGCCGCAGCCGAACG
ACCGAGCGCAGCGAGTCAGTGAGCGAGGAAGCGGAAGAGCGCCCAATACGCAA
ACCGCCTCTCCCCGCGCGTTGGCCGATTCATTAATGCAGCTGGCACGACAGGTTT
CCCGACTGGAAAGCGGGCAGTGAGCGCAACGCAATTAATGTGAGTTAGCTCACT
CATTAGGCACCCCAGGCTTTACACTTTATGCTTCCGGCTCGTATGTTGTGTGGAAT
TGTGAGCGGATAACAATTTCACACAGGAAACAGCTATGACCATGATTACGCCAA
GCTTGCATGCAAATTCTATTTCAAGGAGACAGTCATAATGAAATACCTATTGCCT
ACGGCAGCCGCTGGATTGTTATTACTCGCGGCCCAGCCGGCCATGGCCCAGGTGC
AGCTGCAGGAGTCATAATGAGGGACCCAGGTCACCGTCTCAAGCGACAAGACAC
ACACCTGCCCTCCTTGTCCAGCCCCCGAACTGCTGGGTGGGCCCAGCGTGTTCCT
GTTTCCTCCTAAACCCAAAGCACTCTGATGATTAGTAGGACCCCAGAAGTCACT
TGCGTGGTGGTTGACGTGTCACATGAAGATCCCGAGGTCAAGTTCAATTGGTATG
TTGACGGGGTCGAAGTTCACAACGCTAAAACTAAACCAAGAGAGGAACAGTATA
ACTCTACCTACCGGGTGGTGAGTGTTCTGACTGTCCTCCATCAAGACTGGCTGAA
TGGCAAAGAATACAAGTGTAAGGTGAGCAACAAAGCCCTGCCCGCTCCTATAGA
GAAAACAATATCCAAAGCCAAAGGTCAACCTCGCGAGCCACAGGTGTACACCCT
CCCACCAAGCCGCGATGAACTTACTAAGAACCAAGTCTCTCTTACTTGCCTGGTT
AAGGGGTTCTATCCATCCGACATTGCAGTCGAGTGGGAGTCTAATGGACAGCCTG
AGAACAACTACAAAACCACCCCTCCTGTTCTGGATTCTGACGGATCTTTCTTCCTT
TATTCTAAACTCACCGTGGATAAAAGCAGGTGGCAGCAGGGCAACGTGTTCAGCT
GTTCCGTTATGCATGAGGCCCTGCATAACCATTATACCCAGAAGTCTTTGTCCCTC
AGTCCAGGAAAGGCGGCCGCACATCATCATCCACCATCACGGGGCCGCAGAACAA
AAACTCATCTCAGAAGAGGATCTGAATGGGGCCGCATAGACTGTTGAAAGTTGTT
TAGCAAAACCTCATACAGAAAATTCATTTACTAACGTCTGGAAAGACGACAAAA
CTTTAGATCGTTACGCTAACTATGAGGGCTGTCTGTGGAATGCTACAGGCGTTGT
GGTTTGTACTGGTGACGAAACTCAGTGTTACGGTACATGGGTTCCTATTGGGCTT
GCTATCCCTGAAAATGAGGGTGGTGGCTCTGAGGGTGGCGGTTCTGAGGGTGGC
GGTTCTGAGGGTGGCGGTACTAAACCTCCTGAGTACGGTGATACACCTATTCCGG
GCTATACTTATATCAACCCTCTCGACGGCACTTATCGCCTGGTACTGAGCAAAA
CCCCGCTAATCCTAATCCTTCTCTTGAGGAGTCTCAGCCTCTTAATACTTTCATGT
TTCAGAATAATAGGTTCCGAAATAGGCAGGGTGCATTAACTGTTTATACGGGCAC
TGTTACTCAAGGCACTGACCCCGTTAAAACTTATTACCAGTACACTCCTGTATCAT
CAAAAGCCATGTATGACGCTTACTGGAACGGTAAATTCAGAGACTGCGCTTTCCA
TTCTGGCTTTAATGAGGATCCATTCGTTTGTGAATATCAAGGCCAATCGTCTGACC
TGCCTCAACCTCCTGTCAATGCTGGCGGCGGCTCTGGTGGTGGTTCTGGTGGCGG
CTCTGAGGGTGGCGGCTCTGAGGGTGGCGGCTCTGAGGGTGGCGGTTCTGAGGGT
GGCGGCTCTGAGGGTGGCGGTTCCGGTGGCGGCTCCGGTTCCGGTGATTTTGATT
ATGAAAAAATGGCAAACGCTAATAAGGGGGCTATGACCGAAAATGCCGATGAAA
ACGCGCTACAGTCTGACGCTAAAGGCAAACTTGATTCTGTCGCTACTGATTACGG
TGCTGCTATCGATGGTTTCATTGGTGACGTTTCCGGCCTTGCTAATGGTAATGGTG
CTACTGGTGATTTTGCTGGCTCTAATTCCCAAATGGCTCAAGTCGGTGACGGTGA
TAATTCACCTTTAATGAATAATTTCCGTCAATATTTACCTTCTTTGCCTCAGTCGG
TTGAATGTCGCCCTTATGTCTTTGGCGCTGGTAAACCATATGAATTTTCTATTGAT
TGTGACAAAATAAACTTATTCCGTGGTGTCTTTGCGTTTCTTTTATATGTTGCCAC
CTTTATGTATGTATTTTCGACGTTTGCTAACATACTGCGTAATAAGGAGTCTTAAT
AAGAATTCACTGGCCGTCGTTTTACAACGTCGTGACTGGGAAAACCCTGGCGTTA
CCCAACTTAATCGCCTTGCAGCACATCCCCCTTTCGCCAGCTGGCGTAATAGCGA
AGAGGCCCGCACCGATCGCCCTTCCCAACAGTTGCGCAGCCTGAATGGCGAATG
GCGCCTGATGCGGTATTTTCTCCTTACGCATCTGTGCGGTATTTCACACCGCATAC
GTCAAAGCAACCATAGTACGCGCCCTGTAGCGGC
```

SEQ ID NO: 7-pDCL5

```
GAGTGAGCTGATACCGCTCGCCGCAGCCGAACGACCGAGCGCAGCGAGTCAGTG
AGCGAGGAAGCGGAAAAACGCCCAATACGCAAACCGCCTCTTCCCCGCGCGTTG
GCCGATTCATTAATGCAGCGTCGACACTGCGGGGCTCTGGAGACGACTTACGGT
AAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGG
AGTATTTACGGTAAACTGCCCACTTGGCAGTACATCAAGTGTATCATATGCCAAG
TCCGCCCCCTATTGACGTCAATGACGGTAAATGGCCCGCCTGGCATTATGCCCAG
TACATGACCTTACGGGACTTTCCTACTTGGCAGTACATCTACGTATTAGTCATCGC
TATTACCATGCTGATGCGGTTTTGGCAGTACACCAATGGGCGTGGATAGCGGTTT
GACTCACGGGGATTTCCAAGTCTCCACCCCATTGACGTCAATGGGAGTTTGTTTT
GGCACCAAAATCAACGGGACTTTCCAAAATGTCGTAATAACCCCGCCCCGTTGAC
GCAAATGGGCGGTAGGCGTGTACGGTGGGAGGTCTATATAAGCAGAGCTCGTTT
AGTGAACCGTCAGATCGCCTGGAGAGGCCATCCACGCTGTTTTGACCTCCATAGT
GGACACCGGGACCGATCCAGCCTCCGCGGCCGGGAACGGTGCATTGGAACGCGG
ATTCCCCGTGCCAAGAGTGACCCTGGCAGAACTCGGTAAGTCTGTTGACATGTAT
```

SEQUENCE LISTING/COMPUTER PROGRAM LISTING

Here we list the SEQENCE IDs referred to in the text

```
GTGATGTATACTAACCTGCATGGGACGTGGATTTACTTGTGTATGTCAGATAGAG
TAAAGATTAACTCTTGCATGTGAGCGGGGCATCGAGATAGCGATAAATGAGTCA
GGAGGACGGATACTTATATGTGTTGTTATCCTCCTCTACAGTCAAACAGATTAAG
CGTCTCAGGGGTGGCACGACAGGTTTCCCGACTGGAAAGCGGGCAGTGAGCGCA
ACGCAATTAATGTGAGTTAGCTCACTCATTAGGCACCCCAGGCTTTACACTTTAT
GCTTCCGGCTCGTATGTTGTGTGGAATTGTGAGCGGATAACAATTACGGTTTCCC
TCTAGAAATAATTTTGTTTAACAGGAGGTGCCACCATGATGAAATTTACTGTCGT
CGCTGCTGCGTTGTTGTTGGGTGCAGTGCGCGCAATGTAAGTAACTAACTAG
CTGTGTGAGAACAGGCTACGAAATCCCCTGTGGATGACTGGCAAGTCGTTGTTGG
CCACCAATCTTACACCACCGTTATAGTCGGACGCCTGTAGTGCAAGTGCACCGCG
CGATGGTCCTTACGGGTTACTGACGCCATTCTGTCCTCCCATCTGATCTATGCGAA
ACCGCCTCATCGTGCAGGTCACCGTCTCCTCAGACAAGACCCACACGTGCCCGCC
GTGCCCGGCCCCGGAGCTCCTGGGCGGTCCTTCCGTGTTCCTCTTTCCGCCAAAG
CCGAAAGATACCTTGATGATTAGCAGAACCCCGGAGGTGACGTGCGTCGTGGTC
GACGTGTCCCACGAGGATCCGGAAGTCAAGTTCAATTGGTACGTCGACGGTGTGG
AGGTGCACAACGCCAAGACCAAGCCGAGAGAGGAGCAGTACAACTCCACCTACC
GCGTCGTGAGCGTGCTGACCGTGCTGCACCAAGACTGGTTGAACGGCAAGGAAT
ACAAGTGCAAGGTGTCGAACAAGGCCCTGCCGGCCCCGATCGAAAAGACCATTA
GCAAGGCGAAGGGCCAGCCGCGCGAGCCGCAAGTGTACACCCTCCCGCCATCAC
GGGATGAGCTGACCAAGAACCAGGTGTCCTTGACGTGTCTGGTCAAGGGCTTCTA
CCCGAGCGACATTGCCGTGGAGTGGGAATCCAACGGCCAGCCGGAAAACAACTA
TAAGACCACCCCACCTGTGCTTGACTCCGATGGTTCCTTCTTCCTGTACTCCAAGC
TGACGGTGGATAAGTCCCGCTGGCAGCAGGGTAACGTGTTTAGCTGCTCAGTCAT
GCACGAAGCCCTGCACAACCACTACACCCAGAAGTCACTGTCCCTGTCGCCAGGC
AAAGCGGCGGCGCATCATCATCACCATCACGGGGCCGCAGAACAAAAACTCATC
TCAGAAGAGGATCTGAATGGGGCCGCATAGACTGTTGAAAGTTGTTTAGCAAAA
CCTCATACAGAAAATTCATTTACTAACGTCTGGAAAGACGACAAAACTTTAGATC
GTTACGCTAACTATGAGGGCTGTCTGTGGAATGCTACAGGCGTTGTGGTTTGTAC
TGGTGACGAAACTCAGTGTTACGGTACATGGGTTCCTATTGGGCTTGCTATCCCT
GAAAATGAGGGTGGTGGCTCTGAGGGTGGCGGTTCTGAGGGTGGCGGTTCTGAG
GGTGGCGGTACTAAACCTCCTGAGTACGGTGATACACCTATTCCGGGCTATACTT
ATATCAACCCTCTCGACGGCACTTATCCGCCTGGTACTGAGCAAAACCCCGCTAA
TCCTAATCCTTCTCTTGAGGAGTCTCAGCCTCTTAATACTTTCATGTTTCAGAATA
ATAGGTTCCGAAATAGGCAGGGTGCATTAACTGTTTATACGGGCACTGTTACTCA
AGGCACTGACCCCGTTAAAACTTATTACCAGTACACTCCTGTATCATCAAAAGCC
ATGTATGACGCTTACTGGAACGGTAAATTCAGAGACTGCGCTTTCCATTCTGGCT
TTAATGAGGATCCATTCGTTTGTGAATATCAAGGCCAATCGTCTGACCTGCCTCA
ACCTCCTGTCAATGCTGGCGGCGGCTCTGGTGGTGGTTCTGGTGGCGGCTCTGAG
GGTGGCGGCTCTGAGGGTGGCGGCTCTGAGGGTGGCGGTTCTGAGGGTGGCGGC
TCTGAGGGTGGCGGTTCCGGTGCGGCTCCGGTTCCGGTGATTTTGATTATGAAA
AAATGGCAAACGCTAATAAGGGGGCTATGACCGAAAATGCCGATGAAACGCGC
TACAGTCTGACGCTAAAGGCAAACTTGATTCTGTCGCTACTGATTACGGTGCTGC
TATCGATGGTTTCATTGGTGACGTTTCCGGCCTTGCTAATGGTAATGGTGCTACTG
GTGATTTTGCTGGCTCTAATTCCCAAATGGCTCAAGTCGGTGACGGTGATAATTC
ACCTTTAATGAATAATTTCCGTCAATATTTACCTTCTTTGCCTCAGTCGGTTGAAT
GTCGCCCTTATGTCTTTGGCGCTGGTAAACCATATGAATTTTCTATTGATTGTGAC
AAAATAAACTTATTCCGTGGTGTCTTTGCGTTTCTTTTATATGTTGCCACCTTTAT
GTATGTATTTTCGACGTTTGCTAACATACTGCGTAATAAGGAGTCTTAATAAAAA
ATGGCTAATAAAGGAAATTTATTTTCATTGCAATAGTGTGTTGGAATTTTTTGTGT
CTCTCACTCGGAAGGACATATGGGAGGGCAAATCATTTAAAACATCAGAATGAG
TATTTGGTTTAGAGTTTGGCAACATATGCCCATATGCTGGCTGCCATGAACAAAG
GTTGGCTATAAAGAGGTCATCAGTATATGAAACAGCCCCTGCTGTCCATTCCTT
ATTCCATAGAAAAGCCTTGACTTGAGGTTAGATTTTTTTTATATTTTGTTTTGTGTT
ATTTTTTTCTTTAACATCCCTAAAATTTTCCTTACATGTTTTACTAGCCAGATTTTT
CCTCCTCTCCTGACTACTCCCAGTCATAGCTGTCCCTCTTCTCTTATGGAGATCGA
ATTCACTGGCCGTCGTTTTACAACGTCGTGACTGGGAAAACCCTGGCGTTACCCA
ACTTAATCGCCTTGCAGCACATCCCCCTTTCGCCAGCTGGCGTAATAGCGAAGAG
GCCCGCACCGATCGCCCTTCCCAACAGTTGCGCAGCCTGAATGGCGAATGGCGCC
TGATGCGGTATTTTCTCCTTACGCATCTGTGCGGTATTTCACACCGCATACGTCAA
AGCAACCATAGTACGCGCCCTGTAGCGGCGCATTAAGCGCGGCGGGTGTGGTGG
TTACGCGCAGCGTGACCGCTACACTTGCCAGCGCCTTAGCGCCCGCTCCTTTCGC
TTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAA
CTTGATTTGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGGA
ACAACACTCAACTCTATCTCGGGCTATTCTTTTGATTTATAAGGGATTTTGCCGAT
TTCGGTCTATTGGTTAAAAAATGAGCTGATTTAACAAAAATTTAACGCGAATTTT
AACAAAATATTAACGTTTACAATTTTATGGTGCAGTCTCAGTACAATCTGCTCTG
ATGCCGCATAGTTAAGCCAGCCCCGACACCCGCCAACACCCGCTGACGCGCCCTG
ACGGGCTTGTCTGCTCCCGGCATCCGCTTACAGACAAGCTGTGACCGTCTCCGGG
AGCTGCATGTGTCAGAGGTTTTCACCGTCATCACCGAAACGCGCGAGACGAAAG
GGCCTCGTGATACGCCTATTTTTATAGGTTAATGTCATGATAATAATGGTTTCTTA
GACGTCAGGTGGCACTTTTCGGGGAAATGTGCGCGGAACCCCTATTTGTTTATTT
TTCTAAATACATTCAAATATGTATCCGCTCATGAGACAATAACCCTGATAAATGC
TTCAATAATATTGAAAAAGGAAGAGTATGAGTATTCAACATTTCCGTGTCGCCCT
```

SEQUENCE LISTING/COMPUTER PROGRAM LISTING

Here we list the SEQENCE IDs referred to in the text

```
TATTCCCTTTTTTGCGGCATTTTGCCTTCCTGTTTTTGCTCACCCAGAAACGCTGGT
GAAAGTAAAAGATGCTGAAGATCAGTTGGGTGCCCGAGTGGGTTACATCGAACT
GGATCTCAACAGCGGTAAGATCCTTGAGAGTTTTCGCCCCGAAGAACGTTTTCCA
ATGATGAGCACTTTTAAAGTTCTGCTATGTGGCGCGGTATTATCCCGTATTGACG
CCGGGCAAGAGCAACTCGGTCGCCGCATACACTATTCTCAGAATGACTTGGTTGA
GTACTCACCAGTCACAGAAAAGCATCTTACGGATGGCATGACAGTAAGAGAATT
ATGCAGTGCTGCCATAACCATGAGTGATAACACTGCGGCCAACTTACTTCTGACA
ACGATCGGAGGACCGAAGGAGCTAACCGCTTTTTTGCACAACATGGGGGATCAT
GTAACTCGCCTTGATCGTTGGGAACCGGAGCTGAATGAAGCCATACCAAACGAC
GAGCGTGACACCACGATGCCTGTAGCAATGGCAACAACGTTGCGCAAACTATTA
ACTGGCGAACTACTTACTCTAGCTTCCCGGCAACAATTAATAGACTGGATGGAGG
CGGATAAAGTTGCAGGACCACTTCTGCGCTCGGCCCTTCCGGCTGGCTGGTTTAT
TGCTGATAAATCTGGAGCCGGTGAGCGTGGGTCTCGCGGTATCATTGCAGCACTG
GGGCCAGATGGTAAGCCCTCCCGTATCGTAGTTATCTACACGACGGGGAGTCAGG
CAACTATGGATGAACGAAATAGACAGATCGCTGAGATAGGTGCCTCACTGATTA
AGCATTGGTAACTGTCAGACCAAGTTTACTCATATATACTTTAGATTGATTTAAA
ACTTCATTTTTAATTTAAAAGGATCTAGGTGAAGATCCTTTTTGATAATCTCATGA
CCAAAATCCCTTAACGTGAGTTTTCGTTCCACTGAGCGTCAGACCCCGTAGAAAA
GATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTTCTT
CTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTG
TCTTACCGGGTTGGACTCAAGACGATAGTTACCGGATAAGGCGCAGCGGTCGGG
CTGAACGGGGGGTTCGTGCATACAGCCCAGCTTGGAGCGAACGACCTACACCGA
ACTGAGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCA
CCTCTGACTTGAGCGTCGATTTTTGTGATGCTCGTCAGGGGGCGGAGCCTATGG
AAAAACGCCAGCAACGCGGCCTTTTTACGGTTCCTGGCCTTTTGCTGGCCTTTTGC
TCACATGTTCTTTCCTGCGTTATCCCCTGATTCTGTGGATAACCGTATTACCGCCT
TT
```

SEQ ID NO: 8-delta hinge amino acid
DKTHTCPPCP

SEQ ID NO: 9-delta hinge polynucleotide
GACAAGACCCACACGTGCCCGCCGTGCCCG

SEQ ID NO: 10-eukaryotic expression signal sequence
MGWSCIILFLVATATGVHS

---

The invention claimed is:

1. A triple expression vector for expressing an antibody molecule comprising an Fc domain in prokaryotic and in eukaryotic cells, said triple expression vector comprising:
   a. a polynucleotide encoding an Fc domain protein;
   b. a polynucleotide encoding a phage coat protein;
   c. a cloning site for cloning genes coding an antibody molecule or a part thereof wherein the antibody molecule or part thereof does not comprise an Fc domain;
   d. a prokaryotic secretion signal sequence and a eukaryotic expression signal sequence, or a secretion signal sequence that drives efficient secretion in both prokaryotic and eukaryotic cells;
   e. a promoter for mediating expression in eukaryotic cells; and
   f. a stop codon for preventing expression of the phage coat protein in eukaryotic cells.

2. The triple expression vector of claim 1, further comprising a nucleotide sequence coding a polyadenylation tail.

3. The triple expression vector of claim 1, further comprising a Kozak sequence.

4. The triple expression vector of claim 1, wherein the promoter for mediating expression in eukaryotic cells is a CMV promoter.

5. The triple expression vector of claim 1, further comprising a nucleotide sequence coding an antibody hinge molecule.

6. The triple expression vector of claim 5, wherein the antibody hinge molecule is a portion of a human IgG1 hinge.

7. The triple expression vector of claim 6, wherein the antibody hinge molecule is cysteine free.

8. The triple expression vector of claim 1, further comprising a nucleotide sequence coding an antibody CH2 domain.

9. The triple expression vector of claim 8, wherein the antibody CH2 domain is a human IgG1 CH2 domain.

10. The triple expression vector of claim 1, further comprising a nucleotide sequence coding an antibody CH3 domain.

11. The triple expression vector of claim 10, wherein the antibody CH3 domain is a human IgG1 CH3 domain.

12. The triple expression vector of claim 1, having cloned therein a nucleotide sequence coding an antibody molecule or part thereof wherein the antibody molecule or part thereof does not comprise an Fc domain.

13. A method of building a phage display library of antibody molecules comprising Fc domains, the method comprising the steps of:
   (i) cloning nucleotide sequences coding antibody molecules into the vector of claim 1, wherein the antibody molecules do not comprise Fc domains;
   (ii) combining the vector obtained in step (i) with a helper phage;
   (iii) expressing the antibody molecules comprising Fc domains in the coats of phage particles.

14. The method of claim 13, wherein the antibody molecules comprising the Fc domains are VHH-Fc molecules.

15. The method of claim 13, wherein the antibody molecules comprising the Fc domains are scFv-Fc, VH-Fc or VL-Fc molecules.

16. A method of producing an antibody molecule or part thereof comprising an Fc domain, said method comprising the step of expressing the vector of claim 12 in a prokaryotic cell.

17. The method of claim 16, wherein the vector is expressed on the periplasm of the prokaryotic cell.

18. The method of claim 16, wherein the prokaryotic cell is an E. coli cell.

19. A method of producing an antibody molecule or part thereof comprising an Fc domain, said method comprising the step of expressing the vector of claim 12 in a eukaryotic cell.

20. The method of claim 19, wherein the eukaryotic cell is a mammalian cell.

21. The method of claim 20, wherein the eukaryotic cell is a human cell.

* * * * *